US011708409B2

(12) United States Patent
Lee et al.

(10) Patent No.: US 11,708,409 B2
(45) Date of Patent: Jul. 25, 2023

(54) ANTIBODY OR ANTIGEN-BINDING FRAGMENT THEREOF THAT SPECIFICALLY RECOGNIZES B CELL MALIGNANCIES, CHIMERIC ANTIGEN RECEPTOR COMPRISING SAME, AND USES THEREOF

(71) Applicant: ABCLON INC., Seoul (KR)

(72) Inventors: Jong Seo Lee, Gyeonggi-do (KR); Kyu Tae Kim, Gyeonggi-do (KR); Bong Kook Ko, Seoul (KR); Ki Hyun Kim, Seoul (KR)

(73) Assignee: ABCLON INC., Seoul (KR)

( * ) Notice: Subject to any disclaimer, the term of this patent is extended or adjusted under 35 U.S.C. 154(b) by 117 days.

(21) Appl. No.: 16/956,807

(22) PCT Filed: Dec. 21, 2018

(86) PCT No.: PCT/KR2018/016515
§ 371 (c)(1),
(2) Date: Jun. 22, 2020

(87) PCT Pub. No.: WO2019/125070
PCT Pub. Date: Jun. 27, 2019

(65) Prior Publication Data
US 2021/0061907 A1 Mar. 4, 2021

(30) Foreign Application Priority Data
Dec. 22, 2017 (KR) .................... 10-2017-0178559

(51) Int. Cl.
*C07K 16/28* (2006.01)
*C07K 14/725* (2006.01)
(52) U.S. Cl.
CPC ...... *C07K 16/2803* (2013.01); *C07K 14/7051* (2013.01); *C07K 2317/565* (2013.01); *C07K 2319/03* (2013.01)
(58) Field of Classification Search
CPC ............ C07K 16/2803; C07K 16/2896; C07K 14/7051; C07K 2319/03
See application file for complete search history.

(56) References Cited

U.S. PATENT DOCUMENTS

| 10,246,507 B2 * | 4/2019 | Lee .................... C07K 16/2863 |
| 2005/0070693 A1 | 3/2005 | Hansen et al. |
| 2021/0130490 A1 * | 5/2021 | Lee .................... C07K 14/7051 |

FOREIGN PATENT DOCUMENTS

| CN | 107383196 A | 11/2017 |
| KR | 10-2011-0122859 A | 11/2011 |
| KR | 10-2016-0037667 A | 4/2016 |
| KR | 10-2017-0057298 A | 5/2017 |
| KR | 10-2114631 B1 * | 6/2020 | ............ C07K 16/12 |
| WO | WO-2008/31056 A2 | 3/2008 |
| WO | WO-2014011988 A2 | 1/2014 |
| WO | WO-2015187528 A1 | 12/2015 |
| WO | WO-2016/033570 A1 | 3/2016 |
| WO | WO-2017066136 A3 | 5/2017 |
| WO | WO-2019203600 A1 * | 10/2019 | ............ A61K 35/15 |

OTHER PUBLICATIONS

Sommermeyer, et al. "Fully human CD19-specific chimeric antigen receptors for T-cell therapy", 2017 Macmillan Publishers Limited, part of Springer Nature. Leukemia (2017) 31, 2199-2199 (9 pages).
Extended European Search Report for Application No. 18892983. 01 dated Feb. 17, 2021 (9 pages).
Maude, S. L., et al.; Chimeric Antigen Receptor T Cells for Sustained Remissions in Leukemia, The New England Journal of Medicine, 2014; 371:1507-17.
Topp, M. S., et al.; "Phase II Trial of the Anti-CD19 Bispecific T Cell-Engager Blinatumomab Shows Hematologic and Molecular Remissions in Patients With Relapsed or Refractory B-Precursor Acute Lymphoblastic Leukemia", Journal of Clinical Oncology, vol. 32, No. 36, 2014, pp. 4134-4140.
Nicholson, J. C., et al.; "Construction and Characterisation of a Functional CD19 Specific Single Chain Fv Fragment for Immunotherapy of B Lineage Leukaemia and Lymphoma", Molecular Immunology, vol. 34, No. 16-17, pp. 1157-1165, 1997.
Kochenderfer, J. N., et al.; "Treating B-cell cancer with T cells expressing anti-CD19 chimeric antigen receptors", Nat Rev Clin Oncol. May 2013; 10(5): 267-276.
Porter, D. L., et al.; "Chimeric Antigen Receptor-Modified T Cells in Chronic Lymphoid Leukemia", The New England Journal of Medicine, 2011; 365:725-33.
Kalos, M., et al.; "T Cells with Chimeric Antigen Receptors Have Potent Antitumor Effects and Can Establish Memory in Patients with Advanced Leukemia", Sci Transl Med. 2011, pp. 1-21.
Kochenderfer, J. N., et al..; "Eradication of B-lineage cells and regression of lymphoma in a patient treated with autologous T cells genetically engineered to recognize CD19", Blood, Nov. 18, 2010, vol. 116, No. 20, pp. 4099-4102.
Kochenderfer, J. N., et al, "B-cell depletion and remissions of malignancy along with cytokine-associated toxicity in a clinical trial of anti-CD19 chimeric-antigen-receptor-transduced Tcells", Blood, Mar. 22, 2012, vol. 119, No. 12, pp. 2709-2720.

(Continued)

*Primary Examiner* — Jessica H Roark
(74) *Attorney, Agent, or Firm* — Harness, Dickey & Pierce, P.L.C.

(57) ABSTRACT

The present invention relates to: a novel antibody or an antigen-binding fragment thereof for use in the treatment of cancer by targeting B cell malignancies; a chimeric antigen receptor comprising the same; and uses thereof. The antibody of the present invention is an antibody specifically binding to CD19 highly expressed in cancer cells (particularly, blood cancer) and has very low homology compared to the CDR sequences of conventional CD19 target antibodies, and thus the sequence thereof is unique. In addition, cells expressing a chimeric antigen receptor comprising an anti-CD19 antibody or antigen-binding fragment of the present invention induce immune cell activity in response to a positive cell line expressing CD19, and thus can be usefully used as a therapeutic agent for CAR-immune cells.

9 Claims, 10 Drawing Sheets

Specification includes a Sequence Listing.

(56) References Cited

OTHER PUBLICATIONS

Genbank Acession No. ACF37471.1, Immunoglobulin Heavy Chain Variable Region, Partial [*Homo sapiens*], Jul. 26, 2016.
Genbank Acession No. ALG00303.1, "Anti-HIV-1 Immunoglobulin Light Chain Variable Region, Partial [*Homo sapiens*]," Jun. 21, 2016.
International Search Report from corresponding PCT Application No. PCT/KR2018/016515, dated Apr. 17, 2019.
Office Action from corresponding Chinese Patent Application No. 201880083127.0, dated Jan. 18, 2023.

* cited by examiner

ANTIBODY OR ANTIGEN-BINDING FRAGMENT THEREOF THAT SPECIFICALLY RECOGNIZES B CELL MALIGNANCIES, CHIMERIC ANTIGEN RECEPTOR COMPRISING SAME, AND USES THEREOF

CROSS-REFERENCE TO RELATED APPLICATIONS

This application is a national phase application of PCT Application No. PCT/KR2018/016515, filed on Dec. 21, 2018, which claims the benefit and priority to Korean Patent Application No. 10-2017-0178559, filed on Dec. 22, 2017. The entire disclosures of the applications identified in this paragraph are incorporated herein by references.

FIELD

The present disclosure was made with the support of multiple agencies in South Korea, under Project No. 9991006240, which was conducted under the research project entitled "Trans-Governmental Whole-Cycle New Medicine Development Project" within the project named "Development of New CD19-antibody-based CAR-T therapeutics" by Abclon Co., Ltd under the management of the Korea Drug Development Fund, from 1 Feb. 2018 to 31 Jan. 2019.

The present disclosure relates to a novel antibody or an antigen binding fragment thereof for use in targeting B-cell malignancies to treat cancer, a chimeric antigen receptor comprising the same, and uses thereof.

BACKGROUND

B cell malignancies are tumors generated in B cells, which are a type of cell lineage responsible for the immune system of the body. Such a B cell malignancy breaks a normal immune system to decrease the immunity against antigens invading from the outside, finally causing the death of patients. For example, acute lymphocytic leukemia (ALL), which is one of B cell malignancies, refers to a disease in which the lymphoid line of white blood cells becomes malignant, grows in the bone marrow, and spreads to peripheral blood, thus invading the liver, the spleen, the lymph, the cerebrum, the cerebellum, the spinal cord, and so on. Acute lymphocytic leukemia is predicted to have a global incidence of 161,000 and a death number of 110,000 in 2015, and both outbreaks of acute lymphocytic leukemia and deaths from acute lymphocytic leukemia are more prevalent in men than women. Representative of therapies for acute lymphocytic leukemia are chemotherapy, targeted therapy, and allogeneic stem cell transplantation. These therapies have been improved to carry the survival rate of child patients to over 85%. However, there are patients unresponsive to conventional therapies or patients in recurrence, and acute lymphocytic leukemia is the most common cause of cancer and death from cancer among children.

Most lymphomas/leukemias generated from B cell malignancies as well as acute lymphocytic leukemia are characterized by the expression of CD19 antigen on the surface of the cells. On the basis of this feature, various therapies designed to recognize CD19 antigen have been tried. Such CD19-targeted therapies encompass CAR-T therapies, bispecific antibodies, antibody-drug conjugates, immunotoxins, Fc-engineered antibodies, and the like. Among such CD19-target therapies, CAR-T cell therapies were used for treatment of blood cancer through the cell death induction mechanism thereof as it was found to increase cytotoxicity for target cells in acute leukemia patients unresponsive to conventional therapies. A high cure rate (27 of 30 cases) was reported as a clinical test result of such a therapy.

Under such a background, the present inventors developed an antigen-binding fragment that selectively recognizes CD19 in B cell malignancies and a chimeric antigen receptor bearing the same, and verified that cytotoxic T cells that express the chimeric antigen receptor retain cytotoxicity.

SUMMARY

Technical Problem

The present inventors have conducted intensive and thorough research into development of a novel antibody specifically binding to CD19 and a chimeric antigen receptor using the same, in order to treat B cell malignancies. As a result, the present inventors have verified that CD19_8.1 antibody specifically binds to CD19 antigen and that cytotoxic T cells expressing a chimeric antigen receptor containing a fragment of the antibody retain cytotoxic activity, and then have completed the present disclosure.

Therefore, an aspect of the present disclosure is to provide a novel anti-CD19 antibody and an antigen-binding fragment thereof.

Another aspect of the present disclosure is to provide a chimeric antigen receptor comprising: an extracellular domain comprising an anti-CD19 antibody or an antigen-binding fragment thereof; a transmembrane domain; and an intracellular signaling domain.

Still another aspect of the present disclosure is to provide a cell expressing the chimeric antigen receptor.

Still another aspect of the present disclosure is to provide a pharmaceutical composition comprising the anti-CD19 antibody or the antigen-binding fragment thereof, or the cell expressing the chimeric antigen receptor.

Still another aspect of the present disclosure is to provide a nucleic acid molecule encoding the anti-CD19 antibody or the antigen-binding fragment thereof or the chimeric antigen receptor.

Still another aspect of the present disclosure is to provide a recombinant vector carrying the nucleic acid molecule encoding the antibody or the antigen-binding fragment thereof, or the chimeric antigen receptor.

Still another purpose of the present disclosure is to provide a host cell transformed with the anti-CD19 antibody or the antigen-binding fragment thereof, or the recombinant vector.

Technical Solution

The following are claimed herein.

1. An anti-CD19 antibody or an antigen-binding fragment thereof, comprising:

(a) a heavy chain variable region (VH) comprising a CDRH2 comprising an amino acid sequence represented by General Formula 1 below:

General Formula 1

(SEQ ID NO: 201)

GIYYDX$_6$X$_7$X$_8$X$_9$X$_{10}$X$_{11}$X$_{12}$X$_{13}$SVKG wherein X$_6$ is G, A, or S; X$_7$ is S, T, I, A, D, F, L, or H; X$_8$ is A, T, S, Q, W, I, V, M, N, Y, or H; X$_9$ is R, K S, V, A, Q, L, T, E, D, M, L, F, or P; $X_{10}$ is Y, G, S, or T; $X_{11}$ is Y, W, M, or L; $X_{12}$ is A, S, T, or L; and $X_{13}$ is D, S, G, N, or P; and (b) a light chain variable region (VL) comprising a CDRL1 comprising an amino acid sequence represented by General Formula 2 below:

General Formula 2

$X_1GX_3X_4SNIGSX_{10}X_{11}X_{12}Y$ (SEQ ID NO: 202)

wherein $X_1$ is V, A, G, S, W, N, Y, K, T, H, R, Q, E, or D; $X_3$ is G, H, D, L, T, Q, K, N, S, or M; $X_4$ is V, Y, I, P, V, M, A, L, F, or S; $X_{10}$ is N or A; $X_{11}$ is A or P; and $X_{12}$ is V, T, or L.

2. The anti-CD19 antibody or the antigen-binding fragment thereof of claim 1, wherein the heavy chain variable region comprises a CDRH2 comprising an amino acid sequence represented by General Formula 1-1 below:

General Formula 1-1

$GIYYDX_6X_7X_8X_9YYADSVKG$ (SEQ ID NO: 203)

wherein $X_6$ is G, A, or S; $X_7$ is 5, T, I, A, D, F, L, or H; $X_8$ is A, T, S, Q, W, I, V, M, N, Y, or H; $X_9$ is R, K S, V, A, Q, L, T, E, D, M, L, F, or P.

3. The anti-CD19 antibody or the antigen-binding fragment thereof of claim 1, wherein the light chain variable region comprises a CDRL1 comprising an amino acid sequence represented by General Formula 2-1 below:

General Formula 2-1

$X_1GX_3X_4SNIGSNAVY$ (SEQ ID NO: 204)

wherein $X_1$ is V, A, G, S, W, N, Y, K, T, H, R, Q, E, or D; $X_3$ is G, H, D, L, T, Q, K, N, S, or M; and $X_4$ is V, Y, I, P, V, M, A, L, I, F, or S.

4. The anti-CD19 antibody or the antigen-binding fragment thereof of claim 1, wherein: the heavy chain variable region (VH) further comprises a CDRH1 of SEQ ID NO: 1 and a CDRH3 of SEQ ID NO: 3; and the light chain variable region (VL) further comprises a CDRL2 of SEQ ID NO: 5 and a CDRL3 of SEQ ID NO: 6.

5. The anti-CD19 antibody or the antigen-binding fragment thereof of claim 4, wherein the CDRH2 comprises an amino acid sequence selected from the group consisting of SEQ ID NOS: 2 and 7-48.

6. The anti-CD19 antibody or the antigen-binding fragment thereof of claim 4, wherein the CDRL1 comprises an amino acid sequence selected from the group consisting of SEQ ID NOS: 4 and 49-90.

7. The anti-CD19 antibody or the antigen-binding fragment thereof of claim 4, wherein the CDRH2 and CDRL1, respectively, comprise amino acid sequences of SEQ ID NOS: 2 and 4, SEQ ID NOS: 7 and 49, SEQ ID NOS: 8 and 50, SEQ ID NOS: 9 and 51, SEQ ID NOS: 10 and 52, SEQ ID NOS: 11 and 53, SEQ ID NOS: 12 and 54, SEQ ID NOS: 13 and 55, SEQ ID NOS: 14 and 56, SEQ ID NOS: 15 and 57, SEQ ID NOS: 16 and 58, SEQ ID NOS: 17 and 59, SEQ ID NOS: 18 and 60, SEQ ID NOS: 19 and 61, SEQ ID NOS: 20 and 62, SEQ ID NOS: 21 and 63, SEQ ID NOS: 22 and 64, SEQ ID NOS: 23 and 65, SEQ ID NOS: 24 and 66, SEQ ID NOS: 25 and 67, SEQ ID NOS: 26 and 68, SEQ ID NOS: 27 and 69, SEQ ID NOS: 28 and 70, SEQ ID NOS: 29 and 71, SEQ ID NOS: 30 and 72, SEQ ID NOS: 31 and 73, SEQ ID NOS: 35 and 74, SEQ ID NOS: 33 and 75, SEQ ID NOS: 34 and 76, SEQ ID NOS: 35 and 77, SEQ ID NOS: 36 and 78, SEQ ID NOS: 37 and 79, SEQ ID NOS: 38 and 80, SEQ ID NOS: 39 and 81, SEQ ID NOS: 40 and 82, SEQ ID NOS: 41 and 83, SEQ ID NOS: 42 and 84, SEQ ID NOS: 43 and 85, SEQ ID NOS: 44 and 86, SEQ ID NOS: 45 and 87, SEQ ID NOS: 46 and 88, SEQ ID NOS: 47 and 89, or SEQ ID NOS: 48 and 90.

8. The anti-CD19 antibody or the antigen-binding fragment thereof of claim 1, wherein the heavy chain variable region (VH) comprises an amino acid sequence selected from the group consisting of SEQ ID NOS: 91-133.

9. The anti-CD19 antibody or the antigen-binding fragment thereof of claim 1, wherein the light chain variable region (VL) comprises an amino acid sequence selected from the group consisting of SEQ ID NOS: 134-176.

10. The anti-CD19 antibody or the antigen-binding fragment thereof of claim 1, wherein the heavy chain variable region (VH) and the light chain variable region (VL), respectively, comprise amino acid sequences of SEQ ID NOS: 91 and 134, SEQ ID NOS: 92 and 135, SEQ ID NOS: 93 and 136, SEQ ID NOS: 94 and 137, SEQ ID NOS: 95 and 138, SEQ ID NOS: 96 and 139, SEQ ID NOS: 97 and 140, SEQ ID NOS: 98 and 141, SEQ ID NOS: 99 and 142, SEQ ID NOS: 100 and 143, SEQ ID NOS: 101 and 144, SEQ ID NOS: 102 and 145, SEQ ID NOS: 103 and 146, SEQ ID NOS: 104 and 147, SEQ ID NOS: 105 and 148, SEQ ID NOS: 106 and 149, SEQ ID NOS: 107 and 150, SEQ ID NOS: 108 and 151, SEQ ID NOS: 109 and 152, SEQ ID NOS: 110 and 153, SEQ ID NOS: 111 and 154, SEQ ID NOS: 112 and 155, SEQ ID NOS: 113 and 156, SEQ ID NOS: 114 and 157, SEQ ID NOS: 115 and 158, SEQ ID NOS: 116 and 159, SEQ ID NOS: 117 and 160, SEQ ID NOS: 118 and 161, SEQ ID NOS: 119 and 162, SEQ ID NOS: 120 and 163, SEQ ID NOS: 121 and 164, SEQ ID NOS: 122 and 165, SEQ ID NOS: 123 and 166, SEQ ID NOS: 124 and 167, SEQ ID NOS: 125 and 168, SEQ ID NOS: 126 and 169, SEQ ID NOS: 127 and 170, SEQ ID NOS: 128 and 171, SEQ ID NOS: 129 and 172, SEQ ID NOS: 130 and 173, SEQ ID NOS: 131 and 174, SEQ ID NOS: 132 and 175, SEQ ID NOS: or 133 and 176.

11. The anti-CD19 antibody or the antigen-binding fragment thereof of claim 1, wherein the CDRH2 comprises an amino acid sequence of SEQ ID NO: 190 and the CDRL1 comprises an amino acid sequence of SEQ ID NO: 199 or 200.

12. The anti-CD19 antibody or the antigen-binding fragment thereof of claim 11, further comprising a CDRH3 comprising an amino acid sequence of SEQ ID NO: 191-198.

13. The anti-CD19 antibody or the antigen-binding fragment thereof of claim 11, further comprising a CDRH1 of SEQ ID NO:1, a CDRL2 of SEQ ID NO: 5, and a CDRL3 of SEQ ID NO: 6.

14. A nucleic acid molecule encoding the antibody or the antigen-binding fragment thereof of any one of claims 1 to 13.

15. A recombinant vector carrying the nucleic acid molecule of claim 14.

16. A host cell transformed with the recombinant vector of claim 15.

17. A CD19-specific chimeric antigen receptor, comprising:

(a) an extracellular domain comprising the anti-CD19 antibody or the antigen-binding fragment thereof of any one of claims 1 to 13;

(b) a transmembrane domain; and (c) an intracellular signaling domain.

18. The CD19-specific chimeric antigen receptor of claim 17, wherein the transmembrane domain is a transmembrane domain of a protein selected from the group consisting of the alpha, beta, or zeta chain of the T-cell receptor, CD27, CD28, CD3 epsilon, CD45, [0011] CD4, CD5, CD8(CD8a), CD9, CD16, CD22, CD33, CD37, CD64, CD80, CD86, CD134, CD137, and CD154.

19. The CD19-specific chimeric antigen receptor of claim 17, wherein the intracellular signaling domain is a CD3 (CD3 zeta) chain-derived domain.

20. The CD19-specific chimeric antigen receptor of claim 17, wherein the intracellular signaling domain further comprises a costimulatory molecule selected from the group consisting of OX40 (CD134), CD2, CD27, CD28, CDS, ICAM-1, LFA-1 (CD11a/CD18), and 4-1 BB (CD137).

21. A cell expressing the chimeric antigen receptor of any one of claims 17 to 20.

22. The cell of claim 21, wherein the cell is an immune cell selected from the group consisting of a dendritic cell, a killer dendritic cell, a mast cell, an NK-cell, a B-cell or an inflammatory T-lymphocyte, a cytotoxic T-lymphocyte, a regulatory T-lymphocyte, and a helper T-lymphocyte.

23. A pharmaceutical composition for the prevention or treatment of a disease associated with CD19-expressing cells, an autoimmune disease, or an inflammatory disease, the pharmaceutical composition comprising the antibody or the antigen-binding fragment thereof of any one of claims 1 to 13.

24. The pharmaceutical composition of claim 23, wherein the disease associated with CD19-expressing cells is a B-cell malignancy selected from the group consisting of chronic lymphocytic leukemia (CLL), acute lymphocytic leukemia (ALL), pro-lymphocytic leukemia, hairy cell leukemia, common acute lymphocytic leukemia (CALLA), null-acute lymphoblastic leukemia, non-Hodgkin's lymphoma, diffuse large B cell lymphoma (DLBCL), multiple myeloma, follicular lymphoma, splenic lymphoma, marginal zone lymphoma, mantle cell lymphoma, indolent B cell lymphoma, and Hodgkin's lymphoma.

25. The pharmaceutical composition of claim 23, wherein the autoimmune disease or the inflammatory disease is selected from the group consisting of multiple sclerosis, rheumatoid arthritis, and systemic lupus erythematosus (SLE).

26. A pharmaceutical composition for prevention or treatment of a disease associated with CD19-expressing cells, an autoimmune disease, or an inflammatory disease, the pharmaceutical composition comprising the cell of claim 21 or 22.

27. The pharmaceutical composition of claim 26, wherein the disease associated with CD19-expressing cells is a B-cell malignancy selected from the group consisting of chronic lymphocytic leukemia (CLL), acute lymphocytic leukemia (ALL), pro-lymphocytic leukemia, hairy cell leukemia, common acute lymphocytic leukemia (CALLA), null-acute lymphoblastic leukemia, non-Hodgkin's lymphoma, diffuse large B cell lymphoma (DLBCL), multiple myeloma, follicular lymphoma, splenic lymphoma, marginal zone lymphoma, mantle cell lymphoma, indolent B cell lymphoma, and Hodgkin's lymphoma.

28. The pharmaceutical composition of claim 26, wherein the autoimmune disease or the inflammatory disease is selected from the group consisting of multiple sclerosis, rheumatoid arthritis, and systemic lupus erythematosus (SLE).

29. A nucleic acid molecule encoding the chimeric antigen receptor of claims 17 to 20.

30. A recombinant vector carrying the nucleic acid molecule of claim 26.

31. A host cell transformed with the recombinant vector of claim 27.

32. A method for treatment of a disease associated with CD19-expressing cells, an autoimmune disease, or an inflammatory disease, the method comprising administering the composition of any one of claims 23 to 28 to a subject in need thereof.

33. The method of claim 32, wherein the disease associated with CD19-expressing cells is a B-cell malignancy selected from the group consisting of chronic lymphocytic leukemia (CLL), acute lymphocytic leukemia (ALL), pro-lymphocytic leukemia, hairy cell leukemia, common acute lymphocytic leukemia (CALLA), null-acute lymphoblastic leukemia, non-Hodgkin's lymphoma, diffuse large B cell lymphoma (DLBCL), multiple myeloma, follicular lymphoma, splenic lymphoma, marginal zone lymphoma, mantle cell lymphoma, indolent B cell lymphoma, and Hodgkin's lymphoma.

34. The method of claim 32, wherein the autoimmune disease or the inflammatory disease is selected from the group consisting of multiple sclerosis, rheumatoid arthritis, and systemic lupus erythematosus (SLE).

35. The method of claim 32, wherein the subject is a mammal or a human.

Herein, an antibody according to an aspect of the present disclosure includes CD19_8.1 antibody and modified antibodies thereof undergoing affinity maturation.

The CD19_8.1 antibody, the modified antibodies thereof, or antigen-binding fragments thereof, of the present disclosure, have specific binding ability for CD19, like FMC63, which is an antibody used in a conventional chimeric antigen receptor.

Herein, "FMC63" antibody is an example of murine anti-CD19 monoclonal antibodies (Nicholson et al., Molecular Immunology, 34(16-17): 1157-1165 (1997)). The variable regions of FMC63 monoclonal antibody have been used in CAR tested in clinical trials (e.g., see [Kochenderfer et al., Nature Review Clinical Oncol., 10(5); 267-276 (2013); Porter et al., New Eng. J. Med., 365(8): 725-733 (2011); Kalos et al., Science Translational Medicine, 3(95): 95ra73 (2011); Kochenderfer et al., Blood, 116(20): 4099-4102 (2010); and Kochenderfer et al., Blood, 119(12): 2709-2720 (2012)]).

The antibodies of the present disclosure and the FMC63 antibody specifically bind to the same epitope of CD19.

As used herein, the term "antibody" refers to a specific antibody to CD19, and encompasses not only the whole antibody form but also an antigen-binding fragment of an antibody molecule.

The whole antibody has a structure of two full-length light chains and two full-length heavy chains, and each light chain is linked to heavy chain via a disulfide bond. There are gamma (γ), mu (μ), alpha (α), delta (δ), and epsilon (ε) types in heavy chain constant regions, and gamma1 (γ1), gamma2 (γ2), gamma3 (γ3), gamma4 (γ4), alpha1 (α1), and alpha2 (α2) in subclasses thereof. There are kappa (κ) and lambda (λ) types of light chain constant region.

As used herein, the term "antigen-binding fragments" refers to a fragment that retains the function of binding to an antigen and includes Fab, F(ab'), F(ab')2, and Fv. Out of the antibody fragments, Fab (fragment antigen binding) has a structure of having a variable domain of each of the heavy and light chains, a constant domain of the light chain, and the first constant domain (CH1) of the heavy chain, and thus contains one antigen-binding site. Fab' is different from Fab in that the former has a hinge region including at least one cysteine residue at the C-terminal of the CH1 domain of a heavy chain. F(ab')2 is produced by a disulfide bond formation between cysteine residues in the hinge regions of Fab' fragments. Fv is an antibody fragment composed only of variable regions of heavy and light chains, which may be produced by a recombinant technology disclosed in the art. In Fv (two-chain Fv), variable regions of light and heavy chains are linked by a non-covalent bond, and in a single-chain variable fragment (scFv), variable regions of light and heavy chains are linked by a covalent bond through a peptide linker or they may form a dimer structure like a double-chain FV through a direct linkage at the C-terminal. These antibody fragments can be obtained using proteinase (for example, a whole antibody may be subjected to restriction digestion with a papain to obtain Fab fragments or with pepsin to obtain F(ab')2 fragment) or preferably constructed using a recombinant DNA technology.

In the present disclosure, examples of the antibody include a monoclonal antibody, a multi-specific antibody, a human antibody, a humanized antibody, a chimeric antibody, a single-chain Fv (scFv), a single-chain antibody, an Fab fragment, an F(ab') fragment, a disulfide-linked Fv (sdFv), an anti-idiotype (anti-Id) antibody, and epitope-binding fragments of the foregoing antibodies, but are not limited thereto.

As used herein, the term "heavy chain" refers to a full length chain comprising three constant regions CH1, CH2, and CH3 and one variable region VH comprising an amino acid sequence which is sufficient for conferring specificity to an antigen as well fragments thereof. Also, the term "light chain" as used herein refers to a full length chain comprising one constant region CL and one variable region VL comprising an amino acid sequence which is sufficient for conferring specificity to an antigen as well fragments thereof.

The term "variable region" or "variable domain", as used herein refers to a domain of a heavy or a light chain of an antibody, which is responsible for binding the antibody to an antigen. Variable domains of the heavy and light chains of a native antibody (VH and VL, respectively) generally have similar structures, and each include four conserved framework regions (FRs) and three hypervariable regions (HVRs) (Kindt et al., Kuby Immunology, 6th edition, W.H. Freeman and Co., page 91 (2007)).

As used herein, the term "complementarity determining region (CDR)" refers to an amino acid sequence of the hypervariable regions of the immunoglobulin heavy and light chains (Kabat et al., Sequences of Proteins of Immunological Interest, 4th Ed., U.S. Department of Health and Human Services, National Institutes of Health (1987)). Three CDRs are included in each of the heavy chain (CDRH1, CDRH2, and CDRH3) and the light chain (CDRL1, CDRL2, and CDRL3). CDRs provide important contact residues with which the antibody binds to an antigen or an epitope.

As used herein, the term "framework" or "FR" refers to variable domain residues other than hypervariable region (HVR) residues. The FR of the variable domain is generally composed of four FR domains: FR1, FR2, FR3, and FR4. Thus, the HVR and FR sequences generally appear in the following sequence in VH:

FRH1 (framework region 1 of heavy chain)-CDRH1 (complementarity determining region 1 of heavy chain)-FRH2-CDRH2-FRH3-CDRH3-FRH4.

Also, HVR and FR sequences in VL (or Vk) are arranged in the order as follows:

FRL1 (framework region 1 of light chain)-CDRL1 (complementarity determining region 1 of light chain)-FRL2-CDRL2-FRL3-CDRL3-FRL4.

As used herein, the term "specifically binding" or wordings relevant thereto, it is intended that an antibody or a constituent thereof, such as an antigen-binding fragment or scFv, forms a complex with an antigen that is relatively stable under physiologic conditions. Specific binding can be characterized by an equilibrium dissociation constant of at least about $1 \times 10^{-6}$ M or less (e.g., less KD means more strong binding). Methods for determining whether two molecules specifically bind are well known in the art and include, for example, equilibrium dialysis, surface plasmon resonance, and the like.

The term "affinity" refers to the strength of the sum total of noncovalent interactions between a single binding site of a molecule (e.g., an antibody) and its binding partner (e.g., an antigen). Unless indicated otherwise, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein.

The term "human antibody" or "humanized antibody" as used herein refers to an antibody that possesses an amino acid sequence which corresponds to that of an antibody produced by a human or a human cell or derived from a non-human source that utilizes human antibody repertoires or other human antibody-encoding sequences.

The term "chimeric antibody" refers to an antibody in which a portion of the heavy and/or light chain is derived from a particular source or species while the remainder of the heavy and/or light chain is derived from a different source or species.

The anti-CD19 antibody or the antigen-binding fragment thereof according to the present disclosure, as understood by a person skilled in the art, may include variants of the amino acid sequences thereof within the scope that the CD19 can be specifically recognized. For example, a variation may be given to the amino acid sequence of an antibody in order to improve the binding affinity and/or other biological properties of the antibody. The variation includes a deletion, an addition, and/or a substitution of an amino acid residue in the amino acid sequence of the antibody.

Such amino acid variations may be provided on the basis of a relative similarity of amino acid side chains, e.g., hydrophobicity, hydrophilicity, charge, and size. As analyzed for size, shape, and type of amino acid side chains, it is clear that all of arginine, lysine and histidine residues are positively charged; alanine, glycine, and serine are similar in size; phenylalanine, tryptophan, and tyrosine have similar shapes. Accordingly, based on this consideration, arginine, lysine and histidine; alanine, glycine and serine; and phenylalanine, tryptophan and tyrosine may be considered to be biologically functional equivalents.

In making such variations, the hydropathic index of amino acids may be considered. Each amino acid has been assigned a hydropathic index on the basis of their hydrophobicity and charge characteristics: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art. It is known that similar biological activity is retained only upon substitution of certain amino acids for other amino acids having a similar hydropathic index. In making variations based upon the hydropathic index, the substitution of amino acids whose hydropathic indices are within ±2 is preferred, those which are within ±1 are particularly preferred, and those within ±0.5 are even more particularly preferred.

It is well known that substitutions between amino acids having similar hydrophilicity values may result in the generation of proteins having biologically equivalent activities. As disclosed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making variations based upon similar hydrophilicity values, the substitution of amino acids whose hydrophilicity values are within ±2 is preferred, those which are within ±1 are particularly preferred, and those within ±0.5 are even more particularly preferred.

The amino acid exchanges in a protein that do not substantially change the activity of the molecule are well known in the art (H. Neurath, R. L. Hill, The Proteins, Academic Press, New York, 1979). The most common exchanges are found between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

According to one aspect of the present invention, there is provided an anti-CD19 antibody or an antigen-binding fragment thereof, comprising:

(a) a heavy chain variable region (VH) comprising a CDRH2 comprising an amino acid sequence represented by General Formula 1 below:

General Formula 1
(SEQ ID NO: 201)
GIYYDX$_6$X$_7$X$_8$X$_9$X$_{10}$X$_{11}$X$_{12}$X$_{13}$SVKG wherein X$_6$ is G, A, or S; X$_7$ is S, T, I, A, D, F, L, or H; X$_8$ is A, T, S, Q, W, I, V, M, N, Y, or H; X$_9$ is R, K S, V, A, Q, L, T, E, D, M, L, F, or P; X$_{10}$ is Y, G, S, or T; X$_{11}$ is Y, W, M, or L; X$_{12}$ is A, S, T, or L; and X$_{13}$ is D, S, G, N, or P; and (b) a light chain variable region (VL) comprising a CDRL1 comprising an amino acid sequence represented by General Formula 2 below:

General Formula 2
(SEQ ID NO: 202)
X$_1$GX$_3$X$_4$SNIGSX$_{10}$X$_{11}$X$_{12}$Y wherein X$_1$ is V, A, G, S, W, N, Y, K, T, H, R, Q, E, or D; X$_3$ is G, H, D, L, T, Q, K, N, S, or M; X$_4$ is V, Y, I, P, V, M, A, L, F, or S; X$_{10}$ is N or A; X$_{11}$ is A or P; and X$_{12}$ is V, T, or L.

The symbols herein, such as "X$_n$" and "X$_m$", are used to indicate amino acids at positions n and m in the general formulas defined above. In this regard, n and m are integers that indicate the positions of amino acids in the sequence as counted from the N-terminal of the sequence. For example, X$_1$ and X$_6$ indicate the amino acids at positions 1 and 6, respectively, from the N-terminal of the sequence.

In an embodiment of the present disclosure, X$_n$ or X$_m$ are independently selected from a group of possible residues that may be X$_n$ or X$_m$ in the general formulas. A skilled person would appreciate that X$_n$ may be selected from any one of the listed groups of possible residues and that such a selection is independent from the selection of an amino acid in X$_m$, wherein n is different from m. Therefore, any of the listed possible residues at the position of X$_n$ in the general formulas may be independently combined with any of the listed possible residues at any other variable position (at the position of X$_m$).

As described in detail in the examples below, CDRH2 and CDRL1 of the anti-CD19 antibody specifically binding to CD19, the modified antibodies thereof, or the antigen-binding fragments thereof, of the present disclosure, are represented by General Formula 1 or 1-1 and 2 or 2-1, respectively, and the general formulas are created on the basis of the statistical analysis results of a number of randomly modified antibodies. The CD19_8.1 antibody specifically binding to CD19 or the antigen-binding fragment thereof, and the modified antibodies thereof were selected by the verification of an interaction with CD19 through repeated selection tests.

In a specific embodiment of the present disclosure, the heavy chain variable region contained in the anti-CD19 antibody or the antigen-binding fragment thereof of the present disclosure comprises a CDRH2 comprising an amino acid sequence represented by General Formula 1-1 below:

General Formula 1-1
(SEQ ID NO: 203)
GIYYDX$_6$X$_7$X$_8$X$_9$YYADSVKG wherein X$_6$ is G, A, or S; X$_7$ is S, T, I, A, D, F, L, or H; X$_8$ is A, T, S, Q, W, I, V, M, N, Y, or H; X$_9$ is R, K S, V, A, Q, L, T, E, D, M, L, F, or P.

In another specific embodiment of the present disclosure, the light chain variable region contained in the anti-CD19 antibody or the antigen-binding fragment thereof of the present disclosure comprises a CDRL1 comprising an amino acid sequence represented by General Formula 2-1 below:

General Formula 2-1
(SEQ ID NO: 204)
X$_1$GX$_3$X$_4$SNIGSNAVY wherein X$_1$ is V, A, G, S, W, N, Y, K, T, H, R, Q, E, or D; X$_3$ is G, H, D, L, T, Q, K, N, S, or M; and X$_4$ is V, Y, I, P, V, M, A, L, I, F, or S.

In an embodiment of the present disclosure, the heavy chain variable region (VH) contained in the anti-CD19 antibody or the antigen-binding fragment thereof of the present disclosure further comprises a CDRH1 of SEQ ID NO: 1 and a CDRH3 of SEQ ID NO: 3, and the light chain variable region (VL) contained therein further comprises a CDRL2 of SEQ ID NO: 5 and a CDRL3 of SEQ ID NO: 6.

In an embodiment of the present disclosure, the amino acid sequence of CDRH2 represented by the foregoing general formula corresponds to an amino acid sequence selected from the group consisting of SEQ ID NOS: 2 and 7-48.

In an embodiment of the present disclosure, the amino acid sequence of CDRL1 represented by the foregoing general formula corresponds to an amino acid sequence selected from the group consisting of SEQ ID NOS: 4 and 49-90.

In an embodiment of the present disclosure, in the anti-CD19 antibody or the antigen-binding fragment thereof of the present disclosure, the CDRH2 and CDRL1, respectively, comprise amino acid sequences of SEQ ID NOS: 2 and 4, SEQ ID NOS: 7 and 49, SEQ ID NOS: 8 and 50, SEQ ID NOS: 9 and 51, SEQ ID NOS: 10 and 52, SEQ ID NOS: 11 and 53, SEQ ID NOS: 12 and 54, SEQ ID NOS: 13 and 55, SEQ ID NOS: 14 and 56, SEQ ID NOS: 15 and 57, SEQ ID NOS: 16 and 58, SEQ ID NOS: 17 and 59, SEQ ID NOS: 18 and 60, SEQ ID NOS: 19 and 61, SEQ ID NOS: 20 and 62, SEQ ID NOS: 21 and 63, SEQ ID NOS: 22 and 64, SEQ ID NOS: 23 and 65, SEQ ID NOS: 24 and 66, SEQ ID NOS: 25 and 67, SEQ ID NOS: 26 and 68, SEQ ID NOS: 27 and 69, SEQ ID NOS: 28 and 70, SEQ ID NOS: 29 and 71, SEQ ID NOS: 30 and 72, SEQ ID NOS: 31 and 73, SEQ ID NOS: 35 and 74, SEQ ID NOS: 33 and 75, SEQ ID NOS: 34 and 76, SEQ ID NOS: 35 and 77, SEQ ID NOS: 36 and 78, SEQ ID NOS: 37 and 79, SEQ ID NOS: 38 and 80, SEQ ID NOS: 39 and 81, SEQ ID NOS: 40 and 82, SEQ ID NOS: 41 and 83, SEQ ID NOS: 42 and 84, SEQ ID NOS: 43 and 85, SEQ ID NOS: 44 and 86, SEQ ID NOS: 45 and 87, SEQ ID NOS: 46 and 88, SEQ ID NOS: 47 and 89, or SEQ ID NOS: 48 and 90.

In another embodiment of the present disclosure, the heavy chain variable region (VH) of the anti-CD19 antibody or the antigen-binding fragment thereof of the present disclosure comprises an amino acid sequence selected from the group consisting of SEQ ID NOS: 91-133, and/or the light chain variable region (VL) thereof comprises an amino acid sequence selected from the group consisting of SEQ ID NOS: 134-176, but are not limited thereto.

In still another embodiment of the present disclosure, as for the anti-CD19 antibody or the antigen-binding fragment thereof of the present disclosure, the heavy chain variable region (VH) and the light chain variable region (VL), respectively, comprise amino acid sequences of SEQ ID NOS: 91 and 134, SEQ ID NOS: 92 and 135, SEQ ID NOS: 93 and 136, SEQ ID NOS: 94 and 137, SEQ ID NOS: 95 and 138, SEQ ID NOS: 96 and 139, SEQ ID NOS: 97 and 140, SEQ ID NOS: 98 and 141, SEQ ID NOS: 99 and 142, SEQ ID NOS: 100 and 143, SEQ ID NOS: 101 and 144, SEQ ID NOS: 102 and 145, SEQ ID NOS: 103 and 146, SEQ ID NOS: 104 and 147, SEQ ID NOS: 105 and 148, SEQ ID NOS: 106 and 149, SEQ ID NOS: 107 and 150, SEQ ID NOS: 108 and 151, SEQ ID NOS: 109 and 152, SEQ ID NOS: 110 and 153, SEQ ID NOS: 111 and 154, SEQ ID NOS: 112 and 155, SEQ ID NOS: 113 and 156, SEQ ID NOS: 114 and 157, SEQ ID NOS: 115 and 158, SEQ ID NOS: 116 and 159, SEQ ID NOS: 117 and 160, SEQ ID NOS: 118 and 161, SEQ ID NOS: 119 and 162, SEQ ID NOS: 120 and 163, SEQ ID NOS: 121 and 164, SEQ ID NOS: 122 and 165, SEQ ID NOS: 123 and 166, SEQ ID NOS: 124 and 167, SEQ ID NOS: 125 and 168, SEQ ID NOS: 126 and 169, SEQ ID NOS: 127 and 170, SEQ ID NOS: 128 and 171, SEQ ID NOS: 129 and 172, SEQ ID NOS: 130 and 173, SEQ ID NOS: 131 and 174, SEQ ID NOS: 132 and 175, SEQ ID NOS: or 133 and 176.

In order to develop additional antibodies with matured affinity to CD19 antigen as well as the foregoing anti-CD19 antibody or the antigen-binding fragments thereof, the present inventors created a sub-library containing modified CDRH2, CDHR3, and CDRL1 on the basis of the conventionally developed CD19_8.1_2F1. As a result, eight types of affinity-matured antibodies were further derived, and the amino acid sequences of the respective antibodies were listed on the examples and sequence listings of the present disclosure.

The eight types of additional antibodies were derived on the basis of CD19_8.1_2F1, and thus are characterized by comprising CDRH1 of SEQ ID NO: 1, CDRL2 of SEQ ID NO: 5, and CDRL3 of SEQ ID NO: 6.

According to an embodiment of the present disclosure, the anti-CD19 antibody or the antigen-binding fragment thereof comprises a CDRH2 comprising an amino acid sequence of SEQ ID NO: 190 and a CDRL1 comprising an amino acid sequence of SEQ ID NO: 199 or 200.

According to another embodiment of the present disclosure, the anti-CD19 antibody or the antigen-binding fragment thereof comprises a CDRH3 comprising an amino acid sequence selected from SEQ ID NOS: 191-198.

The anti-CD19 antibody or the antigen-binding fragment thereof of the present disclosure includes an anti-CD19 antibody or an antigen-binding fragment thereof that contains a minor change as compared to the foregoing amino acid sequences, that is, a change which does not largely affect the tertiary structure and the functions of the antibody. In some embodiments, the modified anti-CD19 antibody or antigen-binding fragment thereof may have at least 90%, 93%, 95%, or 98% sequence similarity even if not identical to the foregoing sequence.

According to an embodiment of the present disclosure, the anti-CD19 antibody or the antigen-binding fragment of the present disclosure includes a monoclonal antibody, a multispecific antibody, a human antibody, a humanized antibody, a chimeric antibody, a single-chain Fv (scFv), a single-chain antibody, an Fab fragment, an F(ab') fragment, a disulfide-linked Fv (sdFv), an anti-idiotype (anti-Id) antibody, and an epitope-binding fragment thereof, which comprise a heavy chain variable region and a light chain variable region each comprising the foregoing CDR sequences, but are not limited thereto.

In another embodiment of the present disclosure, the anti-CD19 antibody or the antigen-binding fragment of the present disclosure is an anti-CD19 scFv. In a specific embodiment of the present disclosure, In an exemplary embodiment of the present disclosure, the heavy chain variable region and the light chain variable region contained in the antibody or the antigen-binding fragment thereof are linked to each other via a linker, such as (Gly-Ser)n, $(Gly_2$-Ser)n, $(Gly_3$-Ser)n or $(Gly_4$-Ser)n, wherein n is an integer of 1 to 6 and particularly 3 to 4, but is not limited thereto. The light chain variable region and the heavy chain variable region in scFv may be, for example, arranged as follows: light chain variable region-linker-heavy chain variable; or heavy chain variable region-linker-light chain variable region.

The CDR sequence of the antibody of the present disclosure is characteristic since the sequence is very poor similarity to CDR sequences of conventional anti-CD19 antibodies or chimeric antigen receptors including the same. For example, as a result of a BLAST search performed for CD19_8.1 antibody of the present disclosure, the antibody disclosed in U.S. Patent Publication No. 2016/0090427 A1 (SEQ ID NO: 173), which is detected as having the highest similarity, has merely 88.5% CDR sequence similarity to the cd19_8.1 antibody of the present disclosure. Moreover, the antibody disclosed in U. S. Patent Publication 2016/0090427 A1 is a bispecific antibody that specifically binds to VEGF, C-MET, or VEGF and C-MET, and have different targets and types from the antibody of the present disclosure.

According to another aspect of the present disclosure, there is provided a nucleic acid molecule encoding the anti-CD19 antibody or the antigen-binding fragment thereof of the present disclosure.

The term "nucleic acid molecule" as used herein, is intended to encompass DNA (gDNA and cDNA) and RNA molecules. Nucleotides are the basic building block of the nucleic acid molecule and include not only natural nucleotides but also analogues with modified sugars or bases (Scheit, *Nucleotide Analogs*, John Wiley, New York (1980); Uhlman and Peyman, *Chemical Reviews*, 90:543-584 (1990)).

It would be obvious to a person skilled in the art that the nucleotide sequence encoding the antibody or the antigen-biding fragment thereof, or the chimeric antigen receptor polypeptide of the present disclosure is any nucleotide sequence that encodes an amino acid sequence constituting the chimeric antigen receptor molecule and is not limited to a particular nucleotide sequence.

The reason is that even if the nucleotide sequence undergoes mutation, the expression of the mutated nucleotide sequence into a protein may not result in a change in the protein sequence. This is called the degeneracy of codons. Therefore, the nucleotide sequence includes nucleotide sequences containing functionally equivalent codons, codons encoding the same amino acids (e. g., the number of codons for arginine or serine is six, due to the degeneracy of codons), or codons encoding biologically equivalent amino acids.

According to an embodiment of the present disclosure, the nucleotide sequences of polypeptides of heavy chain CDRs, light chain CDRs, heavy chain variable regions, light chain variable regions, heavy chains, or light chains in the antibody to CD19 or the antigen-binding fragment thereof of the present disclosure are listed in the sequence listings appended hereto.

The nucleic acid molecule of the present disclosure which encodes the anti-CD19 antibody or the antigen-binding fragment thereof is construed to also encompass nucleotide sequences having substantial identity to the nucleic acid molecule. In this context, the term "substantial identity" refers to an identity of at least 80%, more preferably at least 90%, and most preferably at least 95% between the nucleotide sequence of the present disclosure and any other sequences as analyzed by commonly used algorithm when alignment therebetween is made as much correspondingly as possible.

Considering the above-described mutations having biologically equivalent activity, it should be construed that nucleic acid molecules encoding the antibody or the antigen-binding fragment or the chimeric antigen receptor polypeptide of the present disclosure also include sequences having substantial identity with the sequences set forth in the sequence listings. In this regard, the substantial identity refers to an identity of at least 61%, more preferably at least 70%, still more preferably 80%, and most preferably at least 90% between the nucleotide sequence of the present disclosure and any other sequences as analyzed by commonly used algorithm when alignment therebetween is made as much correspondingly as possible. Methods of alignment for sequence comparison are known in the art. Various methods and algorithms for alignment are disclosed in Smith and Waterman, *Adv. Appl. Math.* 2:482 (1981); Needleman and Wunsch, *J. Mol. Bio.* 48:443 (1970); Pearson and Lipman, *Methods in Mol. Biol.* 24: 307-31 (1988); Higgins and Sharp, *Gene* 73:237-44 (1988); Higgins and Sharp, *CABIOS* 5:151-3 (1989); Corpet et al., *Nuc. Acids Res.* 16:10881-90 (1988); Huang et al., *Comp. Appl. BioSci.* 8:155-65 (1992) and Pearson et al., *Meth. Mol. Biol.* 24:307-31 (1994). The NCBI Basic Local Alignment Search Tool (BLAST; Altschul, et al., J. Mol. Biol. 215:403-10(1990)) is available from, for example, the NBCI (National Center for Biological Information), and can be used in connection with sequence analysis programs, such as blastp, blasm, blastx, tblastn and tblastx, on the Internet. The use of the program in comparing sequence similarity can be available on the BLAST help page at the NCBI website.

According to still another aspect of the present disclosure, there is provided a recombinant vector carrying a nucleic acid molecule encoding the anti-CD19 antibody or the antigen-binding fragment thereof.

According to still another aspect thereof, there is provided a host cell transformed with the recombinant vector.

Any host cell known in the art can also be used so long as the host cell allows the vector of the present disclosure to be cloned thereto and expressed stably and sequentially. For example, eukaryotic host cells suitable for the vector include monkey kidney cells (COS7), NSO cells, SP2/0, Chinese hamster ovary (CHO) cells, W138, baby hamster kidney (BHK) cells, MDCK, myeloma cell lines, HuT 78 cells, and HEK-293 cells, but are not limited thereto.

According to still another aspect thereof, there is provided a CD19-specific chimeric antigen receptor comprising:

(a) an extracellular domain comprising the anti-CD19 antibody or the antigen-binding fragment thereof;

(b) a transmembrane domain; and (c) an intracellular signaling domain.

As used herein, the term "chimeric antigen receptor (CAR)" refers to an artificially constructed hybrid protein or polypeptide that contains an antigen-binding domain (e.g., single-chain variable fragment (scFv)) of an antibody linked to a T-cell signaling or T-cell activating domain. Chimeric antigen receptors have ability to re-induce T-cell specificity and response to selected targets in a non-MHC-restricted manner, by using the antigen-binding function of a monoclonal antibody. The non-MHC-restricted antigen recognition provides CAR-expressing T cells with an ability to recognize antigens irrespective of antigen processing, thus avoiding main tumor escape mechanisms. In addition, when expressed in T cells, CAR does advantageously not dimerize with intrinsic T-cell receptor (TCR) alpha and beta chains.

The chimeric antigen receptor of the present disclosure comprises an extracellular domain comprising an antibody induced against CD19, known as a B lymphocyte antigen, or an antigen-binding fragment thereof. In the present disclosure, the antibody induced against CD19 or the antigen-binding fragment thereof includes the foregoing anti-CD19 antibodies or antigen-binding fragments thereof.

According to an embodiment of the present disclosure, the chimeric antigen receptor of the present disclosure is expressed on cell surfaces. Hence, the chimeric antigen receptor may comprise a transmembrane domain. The transmembrane domain may be derived from natural or synthetic sources known in the art. The transmembrane domain may be, for example, a transmembrane domain of a protein selected from the group consisting of alpha, beta, or zeta chains of T-cell receptor, CD27, CD28, CD3 epsilon, CD45, [0011] CD4, CD5, CD8 (CD8a), CD9, CD16, CD22, CD33, CD37, CD64, CD80, CD86, CD134, CD137, and CD154, but is not limited thereto.

According to a specific embodiment of the present disclosure, the transmembrane domain is a CD8-derived hinge/ transmembrane domain encoded by a nucleotide sequence comprising SEQ ID NO: 177.

The term "intracellular signaling domain" as used herein refers to a functional protein domain that produces a second messenger or functions as an effector in response to the second messenger to intracellular transfer information so as to regulate cellular activity via a defined signaling pathway.

According to another embodiment of the present disclosure, the chimeric antigen receptor of the present disclosure may comprise an intracellular signaling domain. The intracellular signaling domain is responsible for intracellular signaling following the binding of extracellular ligand binding domain to a target (e.g., CD19) causing the activation of the immune cells and immune response. In other words, the signal transducing domain is responsible for the activation of at least one of the normal effector functions of immune cells. For example, the effector function of T cells may be cytotoxic activity or helper activity including the secretion of cytokines. Preferred examples of signal transducing domain for use in a chimeric antigen receptor may be the cytoplasmic sequences of the T-cell receptor and the co-receptor that act in concert to initiate signal transduction following antigen receptor engagement, as well as any derivate or variant of these sequences and any synthetic sequence that has the same functional ability.

According to a specific embodiment, the intracellular signaling domain of the chimeric antigen receptor is a domain derived from CD3 (CD3 zeta) chain.

According to a more specific embodiment, the domain derived from the CD3 (CD3 zeta) chain is a CD3 domain encoded by a nucleotide sequence comprising SEQ ID NO: 180.

According to another specific embodiment of the present disclosure, the intracellular signaling domain of the chimeric antigen receptor further comprises a costimulatory molecule selected from the group consisting of OX40 (CD134), CD2, CD27, CD28, CDS, ICAM-1, LFA-1(CD11a/CD18), and 4-1BB (CD137). The intracellular signaling domain may be obtained or derived from an intracellular signaling molecule known in the art as well as the domain described above, and may include the entirety or a part of the molecule from which the intracellular signaling domain is derived.

According to one specific embodiment of the present disclosure, the costimulatory molecule may be a functional signaling domain obtained from a protein selected from the group consisting of CD28, OX40, 4-1BB (CD137), and/or ICOS (CD278) and, more particularly, a functional signaling domain of CD28 and/or OX40.

According to another embodiment of the present disclosure, the intracellular signaling domain is a functional signaling of 4-1BB, CD28, OX40, CD3 zeta, or a combination thereof. Most specifically, the intracellular signaling domain is a functional signaling domain of CD3 zeta.

According to a more specific embodiment of the present disclosure, the costimulatory molecule containing CD137 is a CD3 domain encoded by a nucleotide sequence including SEQ ID NO: 179.

The transmembrane domain and intracellular signaling domain in the chimeric antigen receptor of the present disclosure may be at least one combination selected from the transmembrane domains and intracellular signaling domains described above. For example, the chimeric antigen receptor of the present disclosure may comprise the CD8a transmembrane domain and the intracellular signaling domains of CD28 and CD3.

According to another aspect of the present disclosure, there is provided a nucleic acid molecule encoding the chimeric antigen receptor described above.

The above-mentioned anti-CD19 antibody or the antigen-binding fragment (polypeptide) thereof, the nucleic acid molecule encoding the same, the chimeric antigen receptor comprising the anti-CD19 antibody or the antigen-binding fragment thereof, and the nucleic acid molecule encoding the chimeric antigen receptor are each in an isolated state.

As used herein, the term "isolated" means altered or removed from the natural/native state. For example, a nucleic acid or a peptide naturally present in a living animal is not "isolated," but the same nucleic acid or peptide partially or completely separated therefrom is "isolated." An isolated nucleic acid or protein can exist in a substantially purified form, or can exist in a non-native environment, such as a host cell.

According to still another aspect thereof, there is provided a recombinant vector carrying the above-mentioned nucleic acid molecule. For the "vector" to be described hereinafter, the antibody or the antigen-binding fragment thereof, or the nucleic acid molecule encoding a chimeric antigen receptor are commonly applied.

The term "vector" is intended to encompass a transfer vector and an expression vector.

As used herein, the term "transfer vector" refers to a composition of matter which comprises an isolated nucleic acid and which can be used to deliver the isolated nucleic acid into the interior of a cell. Examples of the transfer vector include, but are not limited to, linear polynucleotides, polynucleotides associated with ionic or amphiphilic compounds, plasmids, and viruses. More specifically, the transfer vector includes an autonomously replicating plasmid or virus. The term should also be construed to further include non-plasmid and non-viral compounds which facilitate the transfer of nucleic acid into cells, such as, polylysine compounds or liposomes. Examples of viral transfer vectors include, but are not limited to, adenoviral vectors, adeno-associated virus vectors, retroviral vectors, and lentiviral vectors.

The term "expression vector" as used herein refers to a vector carrying a recombinant polynucleotide containing an expression control sequence operatively linked to a nucleotide sequence to be expressed, in order to express a target gene in a host cell. An expression vector carrying sufficient cis-acting elements for expression; other elements for expression can be supplied by the host cell or an in-vitro expression system. Examples of the expression vector include: plasmid vectors; cosmid vectors; and viral vectors, such as bacteriophage vectors, adenoviral vectors, lentiviral vectors, retroviral vectors, and adeno-associated viral vectors. According to a specific embodiment of the present disclosure, a nucleic acid molecule encoding the switch molecule is operatively linked to a promoter in the vector of the present disclosure. As used herein, the term "operatively linked" means a functional linkage between a regulatory sequence for nucleic acid expression (example: a promoter, a signal sequence, or array of positions to which transcriptional factors bind) and other nucleic acid sequences, and by the operatively linkage, the regulatory sequence is able to regulate the transcription and/or translation of the other nucleic acid sequence.

The recombinant vector system of the present disclosure can be constructed using various methods known in the art. With respect to concrete methods, reference may be made to Sambrook et al., Molecular Cloning, A Laboratory Manual, Cold Spring Harbor Laboratory Press (2001), which is incorporated herein by reference.

The vectors of the present disclosure may be constructed as a vector for gene cloning, a vector for protein expression, or a vector for gene transfer. Also, the vectors of the present disclosure may be constructed by using eukaryotic or prokaryotic cells as host cells.

For example, when the vector of the present disclosure is an expression vector and a eukaryotic cell is a host cell, promoters derived from genomes of mammalian cells (e.g., a metallothionein promoter, β-actin promoter, a human hemoglobin promoter, and a human muscle creatine promoter) or promoters derived from mammalian viruses (e.g., an adenovirus late promoter, a vaccinia virus 7.5K promoter, SV40 promoter, a cytomegalovirus promoter, a tk promoter of HSV, a mouse mammary tumor virus (MMTV) promoter, an LTR promoter of HIV, a promoter of moloney virus, a promoter of Epstein Barr Virus (EBV), a promoter of Rous Sarcoma Virus (RSV)) may be used. Generally, the vectors have a polyadenylation sequence as a transcription termination sequence.

According to one embodiment of the present disclosure, when used as a transfer vector, the vector may be "retroviral vector". Retroviruses provide a convenient platform for gene delivery systems. A gene selected for gene delivery can be inserted into a retroviral vector and packaged in retroviral particles. The recombinant retroviral virus can then be delivered to target host cells either in vivo or in vitro. A number of retroviral vectors are known in the art. In a specific embodiment of the present disclosure, the retroviral vector may be a pMT retroviral vector, which is an MLV-based retroviral vector, but is not limited thereto.

According to another embodiment of the present disclosure, the vector may be a lentiviral vector or an adenoviral vector.

The vector of the present disclosure may be fused with other nucleotide sequences to facilitate the purification of the polypeptide or protein expressed therefrom. Examples of the sequence to be fused include glutathione S-transferase (Pharmacia, USA), maltose binding protein (NEB, USA), FLAG (IBI, USA) and 6× His (hexahistidine; Qiagen, USA) and the like. The expression vector of the present disclosure may also contain a selectable marker gene and/or a reporter gene as a selection marker for evaluating the expression of the antibody or the antigen-binding fragment, and the CAR polypeptide bearing the same of the present disclosure. The selectable marker gene may include an antibiotic resistant gene that is typically used in the art, and examples of the selectable maker gene include genes resistant to ampicillin, gentamicin, carbenicillin, chloramphenicol, streptomycin, kanamycin, geneticin, neomycin, and tetracycline. Examples of the reporter gene may include luciferase, beta-galactosidase, chloramphenicol acetyl transferase, and green fluorescent protein genes.

Methods of introducing the recombination vector of the present disclosure and expressing the same into a cell are known in the art. The vector can be readily introduced into a host cell, e.g., mammalian, bacterial, yeast, or insect cells by any method known in the art. For example, the vector can be transferred into a host cell by physical, chemical, or biological means. Examples of the physical means include calcium phosphate precipitation, lipofection, particle bombardment, microinjection, electroporation, and the like. Examples of the chemical means include colloidal dispersion systems, such as macromolecule complexes, nanocapsules, microspheres, beads, and lipid-based systems including oil-in-water emulsions, micelles, mixed micelles, and liposomes. Examples of the biological means include the use of DNA or RNA vectors, such as lentiviral vectors or retroviral vectors.

According to another aspect of the present disclosure, there is provided a cell expressing the above-mentioned chimeric antigen receptor.

In one embodiment of the present disclosure, the cell refers to a cell of hematopoietic origin functionally involved in the initiation and/or execution of an innate and/or adaptive immune response.

The immune cells according to the present disclosure may be derived from stem cells. The stem cells may be adult stem cells, non-human embryonic stem cells, cord blood stem cells, bone marrow stem cells, induced pluripotent stem cells, or hematopoietic stem cells. More specifically, the immune cells may be selected from the group consisting of dendritic cells, killer dendritic cells, mast cells, NK-cells, B-cells or inflammatory T-lymphocytes, cytotoxic T-lymphocytes, regulatory T-lymphocytes, and helper T-lymphocytes, but are not limited thereto.

In the present disclosure, the chimeric antigen receptor-expressing cells are also called effector cells. The effector cells include a population of autologous or allogeneic cells. In other words, the effector cells include a population of autologous or allogeneic cells expressing CAR specific for CD19.

According to an embodiment of the present disclosure, the effector cells include a population of cells transduced or transfected with a vector carrying a nucleic acid molecular encoding a CD19-specific CAR. The transfection or transduction can be achieved by various means known in the art as described above, without limitations.

Hence, according to a specific embodiment of the present disclosure, after being delivered into the effector cells, e.g., T lymphocytes or natural killer cells, the nucleic acid molecule encoding the CD19-specific CAR is transcribed into mRNA, from which a CD19-specific CAR polypeptide is then translated, and expressed on the cell surface.

According to still another aspect of the present disclosure, there is provided a pharmaceutical composition comprising an anti-CD19 antibody or an antigen-binding fragment thereof, or a pharmaceutical composition comprising a cell expressing the chimeric antigen receptor.

The pharmaceutical composition may be provided in the form of a pharmaceutical composition comprising: the anti-CD19 antibody or the antigen-binding fragment thereof of the present disclosure or the cell expressing the chimeric antigen receptor of the present disclosure; and a pharmaceutically acceptable carrier.

When administered in the form of a pharmaceutical composition, the cell expressing the chimeric antigen receptor of the present disclosure may be a cell derived from an animal of the same species as that of the subject, or an autologous cell.

The pharmaceutical composition of the present disclosure may comprise a population of cells expressing the chimeric antigen receptor of the present disclosure.

Since the pharmaceutical composition of the present disclosure uses, as an active ingredient, the anti-CD19 antibody or antigen-binding fragment thereof of the present disclosure or the cell expressing the chimeric antigen receptor of the present disclosure as described above, the overlapping descriptions therebetween are omitted in order to avoid undue redundancy leading to the complexity of this specification.

As will be validated in the following examples, when co-incubated with a CD19 antigen-expressing cell line (RaJi), the chimeric antigen receptor T cells (CD19_8.1 CAR-T cells) bearing the CD19_8.1 antibody fragments of the present disclosure recognize the CD19 antigen on the surface of the CD19-positive cell line (RaJi) to induce the activation of the chimeric antigen receptor. Therefore, the cells of the present disclosure are expected to have advantageous applications in the treatment of CD19 antigen-related diseases.

Diseases that can be prevented or treated by the pharmaceutical composition of the present disclosure are human and mammalian diseases associated with CD19-expressing cells, and the diseases include B-cell malignancies selected from the group consisting of chronic lymphocytic leukemia (CLL), acute lymphocytic leukemia (ALL), pro-lymphocytic leukemia, hairy cell leukemia, common acute lymphocytic leukemia (CALLA), null-acute lymphoblastic leukemia, non-Hodgkin's lymphoma, diffuse large B cell lymphoma (DLBCL), multiple myeloma, follicular lymphoma, splenic lymphoma, marginal zone lymphoma, mantle cell lymphoma, indolent B cell lymphoma, and Hodgkin's lymphoma.

In addition, the diseases include autoimmune diseases and inflammatory diseases associated with inappropriate or enhanced B-cell count and/or activation. Examples of the autoimmune diseases and inflammatory diseases include multiple sclerosis, rheumatoid arthritis, and systemic lupus erythematosus (SLE).

The pharmaceutically acceptable carrier contained in the pharmaceutical composition of the present disclosure is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil, but are not limited thereto. The pharmaceutical composition of the present disclosure may further comprise a lubricant, a wetting agent, a sweetening agent, a flavoring agent, an emulsifier, a suspending agent, a preservative, and the like in addition to the above ingredients. Suitable pharmaceutically acceptable carriers and preparations are described in detail in Remington's Pharmaceutical Sciences (19th ed., 1995).

The pharmaceutical composition of the present disclosure may be administered orally or parenterally, for example, by intravenous injection, subcutaneous injection, intramuscular injection, intraperitoneal injection, intrasternal injection, intratumoral injection, topical administration, intranasal administration, intrapulmonary administration, and rectal administration.

The appropriate dose of the pharmaceutical composition of the present disclosure varies depending on factors, such as a formulating method, a manner of administration, patient's age, body weight, gender, and morbidity, food, a time of administration, a route of administration, an excretion rate, and response sensitivity. An ordinarily skilled practitioner can easily determine and prescribe an effective dose for desired treatment or prevention. According to a preferable embodiment of the present disclosure, the daily dose of the pharmaceutical composition of the present disclosure is 0.0001-100 mg/kg. As used herein, the term "pharmaceutically effective amount" refers to an amount sufficient to prevent or treat the above-described diseases.

As used herein, the term "prevention" refers to a prophylactic or protective treatment of a disease or a disease condition. As used herein, the term "treatment" refers to a reduction, suppression, relief, or eradication of a disease condition.

The pharmaceutical composition of the present disclosure may be formulated into a unit dosage form or may be prepared in a multi-dose container by using a pharmaceutically acceptable carrier and/or excipient according to a method that can be easily implemented by a person having an ordinary skill in the art to which the present disclosure pertains. In this regard, the formulation may be in the form of a solution in an oily or aqueous medium, a suspension, an emulsion, an extract, a pulvis, a suppository, a powder, a granule, a tablet, or a capsule, and may further contain a dispersant or a stabilizer.

The pharmaceutical composition of the present disclosure may further comprise other pharmaceutically active agents or drugs, for example, chemotherapeutic agents, such as asparaginase, busulfan, carboplatin, cisplatin, daunorubicin, doxorubicin, fluorouracil, gemcitabine, hydroxyurea, methotrexate, paclitaxel, rituximab, vinblastine, and vincristine; targeted therapeutic agents, such as bevacizumab and olaparib; and immune checkpoint inhibitors, such as nivolumab and pembrolizumab, in addition to the above-described chimeric antigen receptor-expressing cells, or may be administered in combination therewith.

According to still another aspect of the present disclosure, there is provided a method for treatment of a disease associated with CD19-expressing cells, an autoimmune disease, or an inflammatory disease, the method comprising administering to a subject in need thereof a composition comprising the antibody against CD19 or the antigen-binding fragment thereof; or a composition comprising an effector cell expressing the CD19-specific chimeric antigen receptor.

The disease associated with CD19-expressing cells, the autoimmune disease, or the inflammatory disease, which is a target disease of the method for treatment of the present disclosure, is as defined above for the target diseases of the pharmaceutical composition.

In an embodiment of the present disclosure, the subject is a mammalian animal or a human.

Since the method for the treatment of cancer or inflammatory diseases of the present disclosure employs, as an active ingredient, the antibody or antigen-binding fragment or the effector cell expressing the chimeric antigen receptor as described above, the overlapping descriptions therebetween are omitted to avoid excessive complication of the specification.

Advantageous Effects

The antibody of the present disclosure binds specifically to CD19 that is highly expressed in cancer cells (particularly, blood cancer) and is very poor in CDR sequence similarity to conventional CD19 target antibodies, and thus the antibody of the present disclosure has a characteristic sequence. Furthermore, the cells expressing a chimeric antigen receptor bearing the anti-CD19 antibody or the antigen-binding fragment of the present disclosure induce immune cell activity in response to CD19-positive cell lines expressing CD19, and thus can be advantageously used as CAR-immune cell therapeutics.

DETAILED DESCRIPTION

Figure 1:
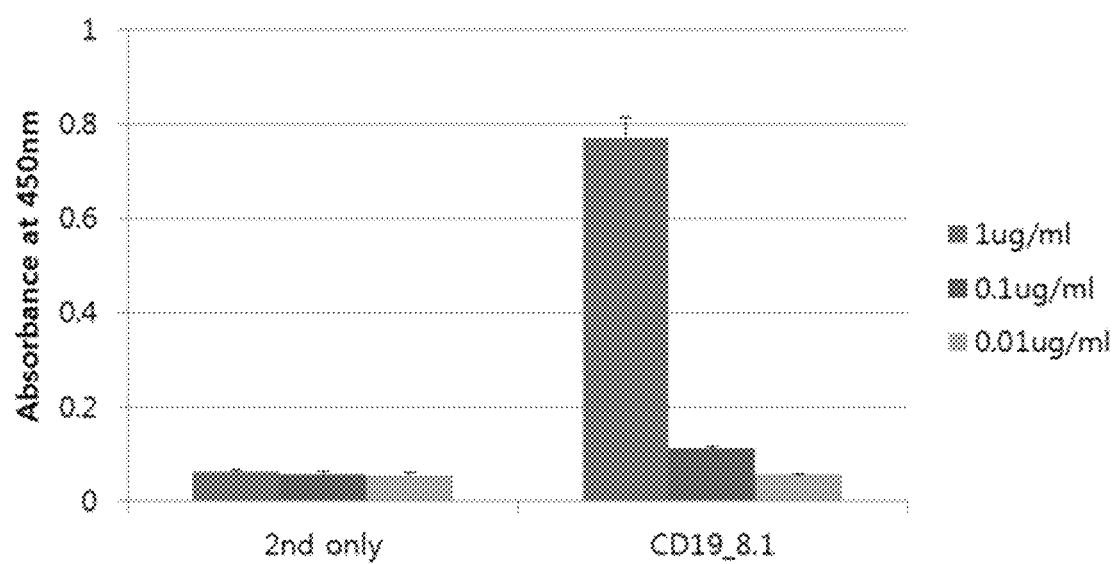
FIG. 1 shows the results of analyzing, through ELISA, the binding of CD19_8.1 antibody fragment to CD19-ECD Fc protein.

Hereinafter, the present disclosure will be described in more detail with reference to examples. These examples are only for illustrating the present disclosure more specifically, and it would be apparent to those skilled in the art that the scope of the present disclosure is not limited by these examples according to the gist of the present disclosure.

EXAMPLES

Example 1: Development of Antibodies to CD19

For antibody development, the extracellular domain (ECD) of human CD19 protein was produced using animal cells, and then used as an antigen. A DNA construct in the form in which the hinge and Fc (CH$_2$—CH$_3$) regions of human IgG1 were conjugated to the C-terminal of ECD was cloned into pCEP4 vector (Invitrogen, USA). Subsequently, the cloned vector was transiently transfected into Free-Style™ 293F cells (Invitrogen, USA) to secure CD19-ECD Fc fusion protein. Phage bio-panning was performed using the CD19-ECD Fc fusion protein and the OPAL library. The antibody library was obtained in a phage form by using VCSM13 helper phage, and used for panning. The number of library phages used to bind to antigens for the first time was $10^{13}$. The panning was carried out up to four panning rounds, and for a panning strategy where high-affinity phages can be selectively well selected, the amount of antigens was reduced and the number of washes was increased as the number of panning rounds was increased. The number of phages binding to target antigens was titrated using *E. coli* ER2537 cells as follows. The binder phages obtained in each round of bio-panning were eluted with a glycine buffer of pH 2.2. The ER2537 cells incubated in SB medium overnight were sub-cultured to a dilution of 1/200 using fresh SB medium. Then, the cells were further incubated at 37° C. for 3 hours to reach the log phage. Then, 100 µl of fresh ER2537 cells and 10 µl of the diluted phages were mixed in a 1.5-ml tube, incubated for 30 minutes, and plated on ampicillin LB plates. After incubation at 37° C. overnight, the number of phages was measured by applying the number of generated colonies and the dilution factor. The binder phages obtained in each round of bio-panning were infected into the ER2537 cells, and while the form of colonies was maintained, the binding to each antigen was examined by ELISA. The colonies obtained by infection with the binder phages were seeded into SB culture medium, and then cultured until the OD$_{600}$ value reached 0.5. Subsequently, 0.5 mM IPTG was added thereto, followed by shaking culture at 30° C., thereby allowing the overexpression of antibody fragment proteins. BBS buffer was used to purify scFv protein. The purified antibody fragments were treated on the CD19-ECD Fc protein-coated plates and the CD19-overexpressed RaJi cell line. After the treatment with the secondary antibody, the TMB color development was induced, and the OD$_{450}$ value was measured using an ELISA reader (Victor X3 PerkinElmer). As for the antibody clones selected as specifically binding to CD19, variable regions thereof were sequenced using a phagemid plasmid and a known primer set (Phage display: a laboratory manual, Carlos Barbas III, et al., Cold Spring Harbor Laboratory Press). Out of the selected antibodies, CD19_8.1 having excellent binding ability to CD19 was selected, and the sequences of variable regions of the selected CD 19_8.1 antibody are shown in Table 1.

TABLE 1

Amino acid sequences of complementarity determining regions (CDRs) of CD19_8.1 antibody

|  | Light chain | Heavy chain |
| --- | --- | --- |
| CDR1 | TGSSSNIGSNAVY (SEQ ID NO: 4) | DYYMS (SEQ ID NO: 1) |
| CDR2 | DDNHRPS (SEQ ID NO: 5) | GIYYDDSSQYYADSVKG (SEQ ID NO: 2) |
| CDR3 | GTWDYSLSGYV (SEQ ID NO: 6) | GPLFCNDRTCSYYYAMDV (SEQ ID NO: 3) |

In order to quantitatively analyze the binding of the selected CD19_8.1 antibody, antibody fragments were produced using animal cells. A DNA construct in the form in which a human kappa light chain region was linked to the C-terminal of the antibody fragment was cloned into Pcep4 vector. Subsequently, the cloned vector was transiently transfected into FreeStyle™ 293F cells, thereby ensuring an antibody in the form of kappa light chain fusion protein. In order to measure the binding ability of the selected antibody, ELISA was performed using CD19-ECD Fc. The plates coated with CD19-ECD Fc protein were treated with the purified antibody fragment in a dose-dependent manner, and treated with secondary antibody, and then the TMB color development was induced, and the $OD_{450}$ value was measured using an ELISA reader (Victor X3 PerkinElmer) (FIG. 1).

Example 2: Affinity Maturation of Developed Antibody Fragments

To secure antibody fragments having excellent binding ability to CD19 compared with CD19_8.1 antibody, a new sub-library was constructed by combining heavy chain and light chain libraries. To create the sub-library, oligonucleotides containing NNK degenerate codons were used. CD19_8.1 antibody fragments were used as template DNA. Randomized codons were introduced in five CDRs except CDRH3 by PCR. Amplified antibody fragments were purified by QIAquick Gel Extraction Kit (QIAGEN, USA). The antibody fragments and pComb3XSS vector were digested with SfiI restriction enzyme, ligated, and then transfected into ER2537, to construct a phage library. On the basis of the constructed phage library, antibodies were selected by the same method as in Example 1.

Figure 2:
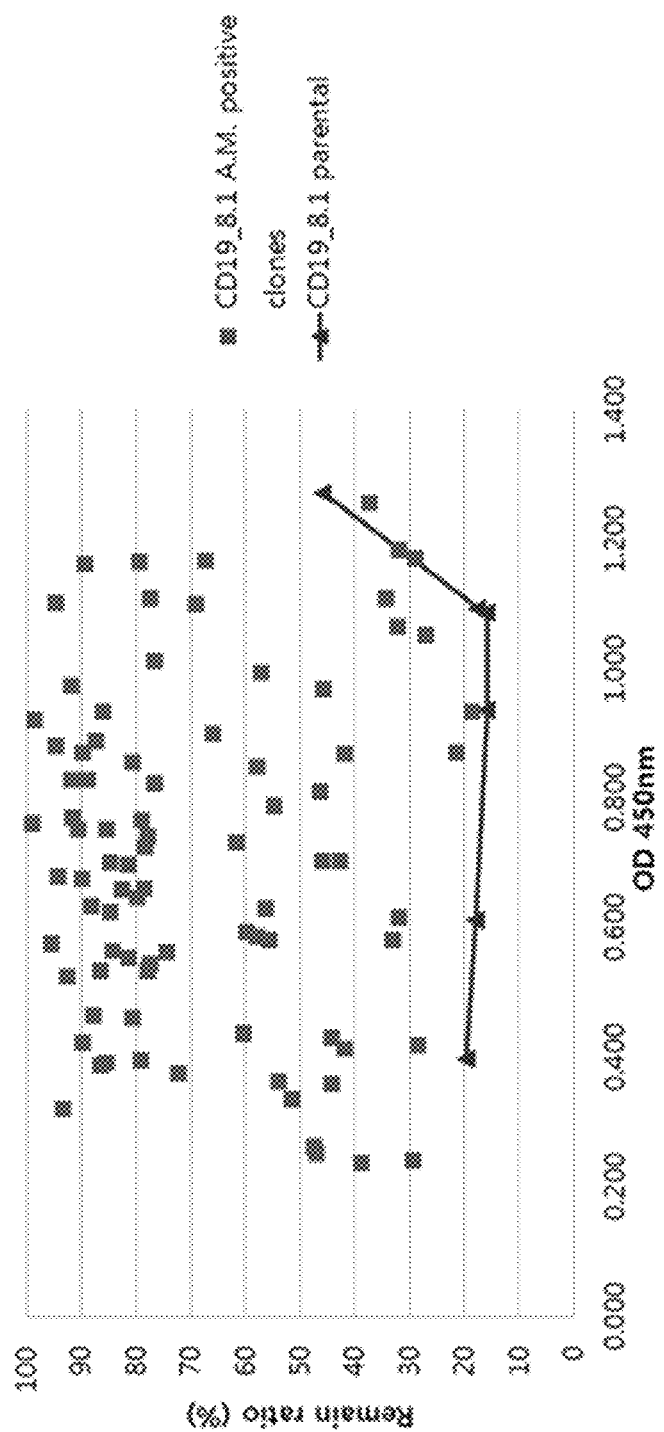
FIG. 2 shows the results of analyzing, through modified ELISA, the binding to CD19-ECD Fc protein, in order to secure affinity-matured antibodies through modifications of the second heavy chain CDR and first light chain CDR regions.

To select antibodies with further matured affinity among the selected antibodies, ELISA was performed using CD19-coated plates. In the performance of ELISA, affinity-matured antibodies were selected by binding of antibody fragments and then incubation at 37° C. for additional 2 hours. The plates were washed after the end of incubation, followed by secondary antibody response and TMB color development, thereby ultimately selecting affinity-matured antibodies. The ELISA results verified that the second heavy chain CDR and the first light chain CDR were important in view of affinity. Therefore, a sub-library having modifications in the second heavy chain CDR and first light chain CDR regions was constructed, and affinity-matured antibodies were selected by the same method as described above (FIG. 2). The antibodies expressed in the selected colonies were sequenced. The sequences of the second heavy chain CDR and first light chain CDR regions, which were variable regions of the selected antibodies, are shown in Table 2.

TABLE 2

Amino acid sequences of second heavy chain CDR and first light chain CDR regions of affinity-matured antibodies

| Antibody | HCDR2 | LCDR1 |
|---|---|---|
| 2B1 | GIYYDGSARYYADSVKG (SEQ ID NO: 7) | VGGVSNIGSNAVY (SEQ ID NO: 49) |
| B12 | GIYYDGSAKYYADSVKG (SEQ ID NO: 8) | AGHYSNIGSNAVY (SEQ ID NO: 50) |
| T2H3 | GIYYDGSAKYYADSVKG (SEQ ID NO: 9) | GGGISNIGSNAVY (SEQ ID NO: 51) |
| T3C1 | GIYYDGSASYYADSVKG (SEQ ID NO: 10) | SGGPSNIGSNAVY (SEQ ID NO: 52) |
| D10 | GIYYDGSAVYYADSVKG (SEQ ID NO: 11) | WGDYSNIGSNAVY (SEQ ID NO: 53) |
| F6 | GIYYDGSAKYYADSVKG (SEQ ID NO: 12) | WGLPSNIGSNAVY (SEQ ID NO: 54) |
| B2 | GIYYDGSTKYYADSVKG (SEQ ID NO: 13) | AGGVSNIGSNAVY (SEQ ID NO: 55) |
| B6 | GIYYDGSTAYYADSVKG (SEQ ID NO: 14) | NGTPSNIGSNAVY (SEQ ID NO: 56) |
| 2F1 | GIYYDGSSQGWSSSVKG (SEQ ID NO: 15) | YGQPSNIGSNAVY (SEQ ID NO: 57) |
| C8 | GIYYDGSQLYYADSVKG (SEQ ID NO: 16) | KGGMSNIGSNAVY (SEQ ID NO: 58) |
| D4 | GIYYDGSSQSMAGSVKG (SEQ ID NO: 17) | TGGVSNIGSNAVY (SEQ ID NO: 59) |
| B5 | GIYYDGSSQGMTNSVKG (SEQ ID NO: 18) | HGTPSNIGSNAVY (SEQ ID NO: 60) |
| G4 | GIYYDGSSQTLLPSVKG (SEQ ID NO: 19) | VGKPSNIGSNAVY (SEQ ID NO: 61) |
| A7 | GIYYDASWTYYADSVKG (SEQ ID NO: 20) | TGNPSNIGSNAVY (SEQ ID NO: 62) |
| D12 | GIYYDASTKYYADSVKG (SEQ ID NO: 21) | RGSASNIGSNAVY (SEQ ID NO: 63) |
| E2 | GIYYDASIRYYADSVKG (SEQ ID NO: 22) | KGMISNIGSNAVY (SEQ ID NO: 64) |
| T2A1 | GIYYDASVKYYADSVKG (SEQ ID NO: 23) | AGKPSNIGSNAVY (SEQ ID NO: 65) |
| T3H9 | GIYYDASAEYYADSVKG (SEQ ID NO: 24) | SGMLSNIGSNAVY (SEQ ID NO: 66) |
| 2G1 | GIYYDSSTRYYADSVKG (SEQ ID NO: 25) | KGSFSNIGSNAVY (SEQ ID NO: 67) |
| C4 | GIYYDSSMRYYADSVKG (SEQ ID NO: 26) | GGQPSNIGSNAVY (SEQ ID NO: 68) |
| C5 | GIYYDSSMRYYADSVKG (SEQ ID NO: 27) | KGGMSNIGSNAVY (SEQ ID NO: 69) |
| D1 | GIYYDSSAKYYADSVKG (SEQ ID NO: 28) | SGGPSNIGSNAVY (SEQ ID NO: 70) |

TABLE 2-continued

Amino acid sequences of second heavy chain CDR and first light chain CDR regions of affinity-matured antibodies

| Antibody | HCDR2 | LCDR1 |
|---|---|---|
| D2 | GIYYDSSTDYYADSVKG (SEQ ID NO: 29) | QGQPSNIGSNAVY (SEQ ID NO: 71) |
| E1 | GIYYDSSVTYYADSVKG (SEQ ID NO: 30) | TGNPSNIGSNAVY (SEQ ID NO: 72) |
| F3 | GIYYDSSARYYADSVKG (SEQ ID NO: 31) | TGSSSNIGSAPLY (SEQ ID NO: 73) |
| T2C1 | GIYYDSSQDYYADSVKG (SEQ ID NO: 32) | RGGPSNIGSNAVY (SEQ ID NO: 74) |
| T2H1 | GIYYDSSQDYYADSVKG (SEQ ID NO: 33) | QGGYSNIGSNAVY (SEQ ID NO: 75) |
| T2H5 | GIYYDSSAKYYADSVKG (SEQ ID NO: 34) | SGNPSNIGSNAVY (SEQ ID NO: 76) |
| T3B8 | GIYYDSSVMYYADSVKG (SEQ ID NO: 35) | EGSPSNIGSNAVY (SEQ ID NO: 77) |
| A12 | GIYYDGTVLYYADSVKG (SEQ ID NO: 36) | QGGPSNIGSNAVY (SEQ ID NO: 78) |
| C2 | GIYYDGTNQYYADSVKG (SEQ ID NO: 37) | TGGLSNIGSNAVY (SEQ ID NO: 79) |
| D7 | GIYYDGTAFYYADSVKG (SEQ ID NO: 38) | EGQPSNIGSNAVY (SEQ ID NO: 80) |
| E3 | GIYYDGTAMYYADSVKG (SEQ ID NO: 39) | SGGYSNIGSNAVY (SEQ ID NO: 81) |
| H10 | GIYYDGTNVYYADSVKG (SEQ ID NO: 40) | LGGYSNIGSNAVY (SEQ ID NO: 82) |
| T3F5 | GIYYDGTAKYYADSVKG (SEQ ID NO: 41) | HGQPSNIGSNAVY (SEQ ID NO: 83) |
| A10 | GIYYDGIYRYYADSVKG (SEQ ID NO: 42) | SGDPSNIGSNAVY (SEQ ID NO: 84) |
| T3H1 | GIYYDGAVQYYADSVKG (SEQ ID NO: 43) | DGGYSNIGSNAVY (SEQ ID NO: 85) |
| B1 | GIYYDGDVRYYADSVKG (SEQ ID NO: 44) | VGSPSNIGSNAVY (SEQ ID NO: 86) |
| B7 | GIYYDGFAPYYADSVKG (SEQ ID NO: 45) | RGTPSNIGSNAVY (SEQ ID NO: 87) |
| D8 | GIYYDGLHQYYADSVKG (SEQ ID NO: 46) | VGNLSNIGSNAVY (SEQ ID NO: 88) |
| E12 | GIYYDSFVPYYADSVKG (SEQ ID NO: 47) | AGSASNIGSNAVY (SEQ ID NO: 89) |
| T2A12 | GIYYDGHQQYYADSVKG (SEQ ID NO: 48) | TGSSSNIGSAPTY (SEQ ID NO: 90) |

Figure 3:
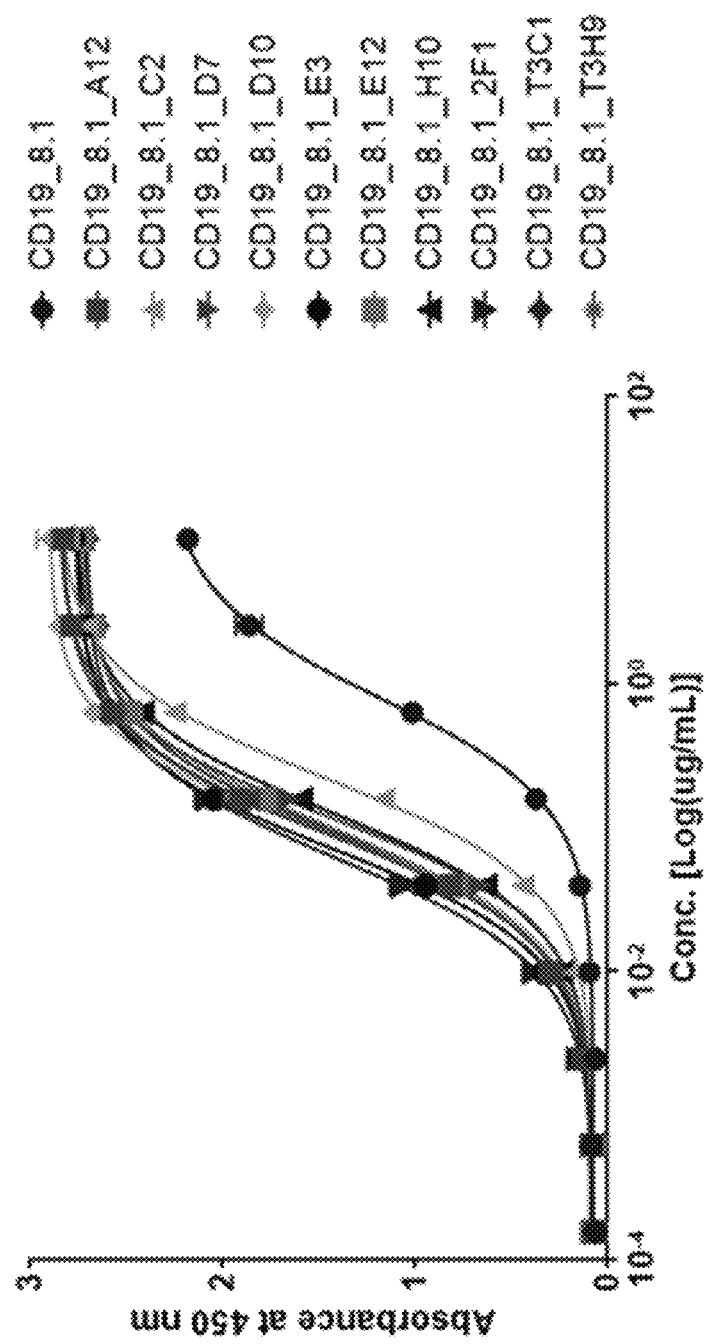
FIG. 3 shows the results of analyzing, through ELISA, the binding of 10 types of affinity-matured antibodies to CD19-ECD Fc protein.

For quantitative testing on 10 types of affinity-matured antibodies among the selected antibodies, antibody fragments were produced by the same method as described in Example 2. As a result, the affinity-matured antibodies were secured as antibodies in the form of kappa light chain fusion protein. To determine the binding ability of the selected antibodies, ELISA was performed using CD19-ECD Fc. The plates coated with CD19-ECD Fc protein were treated with purified antibody fragments in a dose-dependent manner, and treated with secondary antibody, followed by TMB color development, and the $OD_{450}$ value was measured using an ELISA reader (Victor X3 PerkinElmer) (FIG. 3). The measured $OD_{450}$ values were analyzed by Graphpad Prism for the binding ability to CD19-ECD Fc (Table 3).

Figure 4:
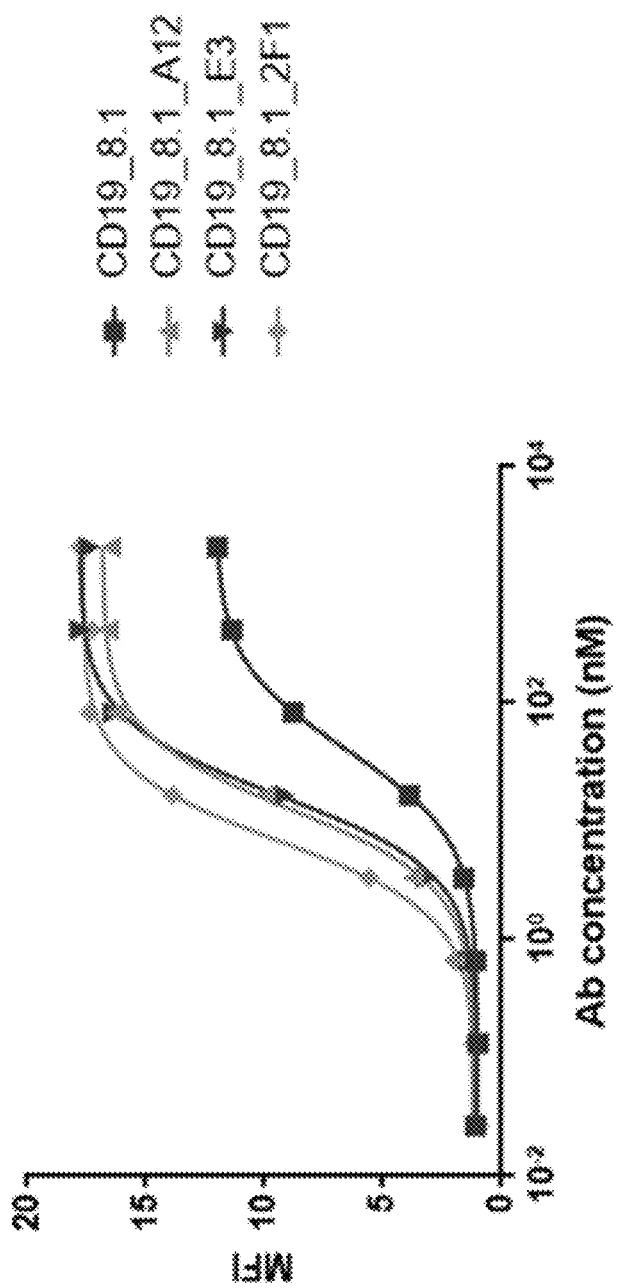
FIG. 4 shows the results of analyzing, through flow cytometry, the binding ability of three types of affinity-matured antibodies to the CD19-positive RaJi cell line.

Out of the selected antibodies, the E3 and 2F1 antibodies with excellent binding ability to CD19-ECD Fc and C2 antibody with relatively low binding ability thereto were investigated for binding ability to the CD19-positive RaJi cell line. The CD19-positive RaJi cell line was treated with purified antibody fragments in a dose-dependent manner, and the antibody fragments binding to the CD19-positive RaJi cell line were stained with anti-human IgG-FITC. The antibody fragments binding to the RaJi cell line were analyzed by flow cytometry (FIG. 4), and the Graphpad Prism was performed for binding ability (Table 4). Through this, antibodies with enhanced binding ability compared with CD19_8.1 were secured.

TABLE 3

Binding ability of 10 types of affinity-matured antibodies to CD19-ECD Fc ($EC_{50}$)

| | CD19_8.1 | A12 | C2 | D7 | D10 | E3 | E12 | H10 | 2F1 | T3C1 | T3H9 |
|---|---|---|---|---|---|---|---|---|---|---|---|
| $EC_{50}$(nM) | 21.04 | 2.37 | 5.81 | 3.20 | 2.48 | 1.87 | 2.56 | 3.31 | 1.60 | 2.40 | 2.32 |

TABLE 4

Binding ability of three types of affinity-matured antibody fragments in RaJi cell line ($EC_{50}$).

| | CD19_8.1 | C2 | E3 | 2F1 |
|---|---|---|---|---|
| $EC_{50}$(nM) | 57.4 | 61.2 | 26.1 | 10.5 |

Example 3: Preparation of Lentivirus Including Developed Antibody Fragment-Linked Chimeric Antigen Receptor A chimeric antigen receptor was developed using the developed antibody CD19_8.1. For the chimeric antigen receptor, codon optimization was made of a CD8 leader, scFv-type CD19_8.1, a hinge domain of CD8, a transmembrane domain and cytoplasmic domain of CD137, and a cytoplasmic domain of CD3 zeta, and the sequence thus optimized was digested with SpeI/XhoI and ligated to pLenti6-V5/DEST lentiviral vector (Invitrogen, USA). The construct thus obtained (SEQ ID NO: 181) was sequenced.

The prepared lentiviral construct was transduced, together with the plasmid pCMV-dR8.91 carrying a nucleic acid encoding vesicular stomatitis Indiana virus G protein (VSV-G), which is a viral coat protein, and the gag, pol, and rev genes, into Lenti-X 293T cells (Takara Bio Inc., Japan). Transduction was performed using Lipofectamine 2000 (Invitrogen, USA) according to the manufacturer's protocol. Seventy-two hours after transduction, a lentivirus-containing culture medium was 10-fold enriched by a centrifugal filter (Millipore, USA), and stored.

Example 4: Preparation of Cytotoxic T Cells Having Developed Antibody Fragment-Linked Chimeric Antigen Receptor Presented on Surface Thereof Cytotoxic T cells having a developed antibody fragment-linked chimeric antigen receptor presented on the surface thereof were prepared using the lentivirus obtained in Example 3.

Figure 5:
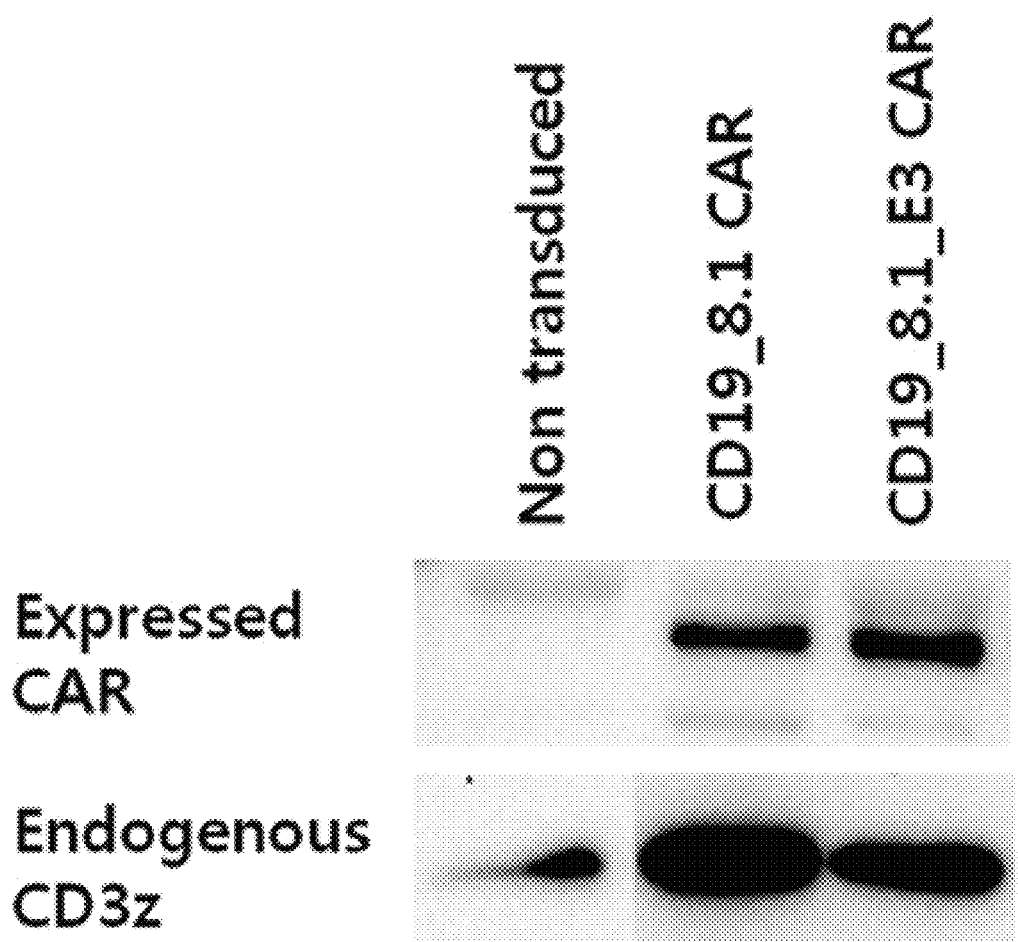
FIG. 5 shows the results of analyzing, through a special protein detection method, the expression of a developed antibody fragment-linked chimeric antigen receptor.

First, human naive T cells were isolated and stimulated with Dynabeads™ Human T-Activator CD3/CD28 (Thermofisher scientific, USA) for 24 hours. Thereafter, the lentivirus containing polybrene (Sigma-Aldrich, USA) was added to the cells and transduced by incubation for 24 hours. Then, the medium was exchanged with a medium containing interleukin-2 (Gibco, USA), followed by incubation at 37° C. in a 5% $CO_2$ atmosphere. The transduction of the CD19_8.1 fragment-linked chimeric antigen receptor was analyzed by CD3z antibody (BD, USA) and a special protein detection method (western blotting) (FIG. 5). The T cells thus prepared, which had the developed CD19_8.1 fragment-linked chimeric antigen receptor presented on the surface thereof, were used in experiments within 24 hours after preparation.

Figure 6:
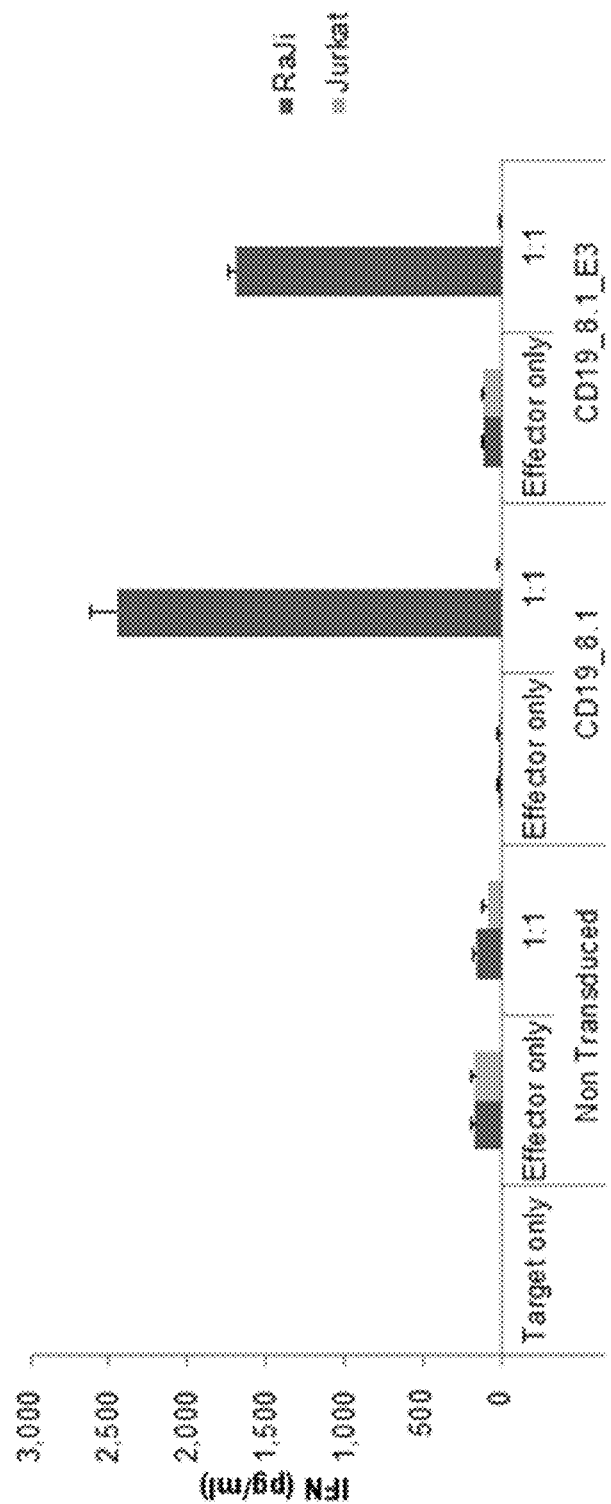
FIG. 6 shows the results of analyzing, through the amount of interferon gamma, the activity of cytotoxic T cells expressing a developed antibody fragment-linked chimeric antigen receptor.

Example 5: Verification on Activity of Cytotoxic T Cells Having Developed Antibody Fragment-Linked Chimeric Antigen Receptor Presented on Surface Thereof The cytotoxic T cells having the chimeric antigen receptor presented on the surface thereof, prepared in Example 3, were used to investigate whether the T cells induce the activation of the chimeric antigen receptor by recognizing CD19 on cell surfaces. Specifically, in the experiments, the CD19-positive RaJi cell line and the CD19-negative Jurkat E6.1 cell line were separately cultured in RPM1-1640 supplemented with 10% fetal bovine serum and 1% penicillin-streptomycin. First, the CD19-positive or negative cells were seeded at a density of $3 \times 10^4$ cells/well into round-bottom 96-well plates. After the removal of the culture supernatant, the prepared chimeric antigen receptor T cells were added according to a treatment ratio per well and incubated at 37° C. for 24 hours in a 5% $CO_2$ atmosphere. As a result, the amount of interferon gamma secreted in the medium was measured using an ELISA kit according to the manufacturer's protocol. The results are shown in FIG. 6. In this regard, a group in which chimeric antigen receptor T cells were added to plates containing no cultured cells (Effector T cell only) and a group in which no chimeric antigen receptor T cells were added to plates containing cultured cells (Target cell only) were used as controls.

As can be seen in FIG. 6, significant increases in the secretion of interferon gamma were detected in the CD19_8.1 antibody fragment-linked chimeric antigen receptor T cells and the CD19-positive cells.

Example 6: Development of Affinity-Matured Antibodies from Developed Antibody Fragments A new sub-library was constructed by combining the second and third heavy chain and first light chain libraries on the basis of CD19_8.1_2F1. To construct the sub-library, oligonucleotides having NNK degenerate codons were used, with 70% or more of the sequence of CD19_8.1_2F1 maintained. The CD19_8.1_2F1 antibody fragment was used as template DNA. The variety using degenerate codons was introduced into three CDRs by PCR. The amplified antibody fragments were purified by QIAquick Gel Extraction Kit (QIAGEN, USA). The amplified antibody fragments and the pComb3XSS vector were digested with SfiI restriction enzyme and ligated, and then transduced into ER2537 to construct a phage library. Antibodies were selected on the basis of the constructed phage library by the same method as in Example 1. Amino acid sequences of variable regions in heavy and light chains of the developed antibodies are shown in Table 5.

TABLE 5

Amino acid sequences of heavy chain CDR and light chain CDR of antibodies derived from 2F1-based sub-library

| Antibody | Second heavy chain CDR | Third heavy chain CDR | First light chain CDR |
|---|---|---|---|
| CD19_8.1_3C12 | GIYYDGSAKYYADSVKG (SEQ ID NO: 190) | GPNFCNDRTCSYYYAMDV (SEQ ID NO: 191) | YGQPSNIGSNAVY (SEQ ID NO: 199) |
| CD19_8.1_6F10 | GIYYDGSAKYYADSVKG (SEQ ID NO: 190) | GPLFCNDRTCSYYYAMDV (SEQ ID NO: 192) | YGQPSNIGSNAVY (SEQ ID NO: 199) |

TABLE 5-continued

Amino acid sequences of heavy chain CDR and light chain CDR of antibodies derived from 2F1-based sub-library

| Antibody | Second heavy chain CDR | Third heavy chain CDR | First light chain CDR |
| --- | --- | --- | --- |
| CD19_8.1_7D2 | GIYYDGSAKYYADSVKG (SEQ ID NO: 190) | GPLFCNDNTCSYYYAMDV (SEQ ID NO: 193) | YGQPSNIGSNAVY (SEQ ID NO: 199) |
| CD19_8.1_7H11 | GIYYDGSAKYYADSVKG (SEQ ID NO: 190) | GPLFCNDDTCSYYYAMDV (SEQ ID NO: 194) | YGQPSNIGSNAVY (SEQ ID NO: 199) |
| CD19_8.1_8E8 | GIYYDGSAKYYADSVKG (SEQ ID NO: 190) | GPLFCNDRDCSYYYAMDV (SEQ ID NO: 195) | YGQPSNIGSNAVY (SEQ ID NO: 199) |
| CD19_8.1_10D3 | GIYYDGSAKYYADSVKG (SEQ ID NO: 190) | GPLFCNDRTCSMYYAMDV (SEQ ID NO: 196) | TGGPSNIGSNAVY (SEQ ID NO: 199) |
| CD19_8.1_10E5 | GIYYDGSAKYYADSVKG (SEQ ID NO: 190) | GPLFCNDRTCSMYYAMDV (SEQ ID NO: 197) | YGQPSNIGSNAVY (SEQ ID NO: 200) |
| CD19_8.1_10H4 | GIYYDGSAKYYADSVKG (SEQ ID NO: 190) | GPLFCNDRTCSKYYAMDV (SEQ ID NO: 198) | YGQPSNIGSNAVY (SEQ ID NO: 199) |

Figure 7:
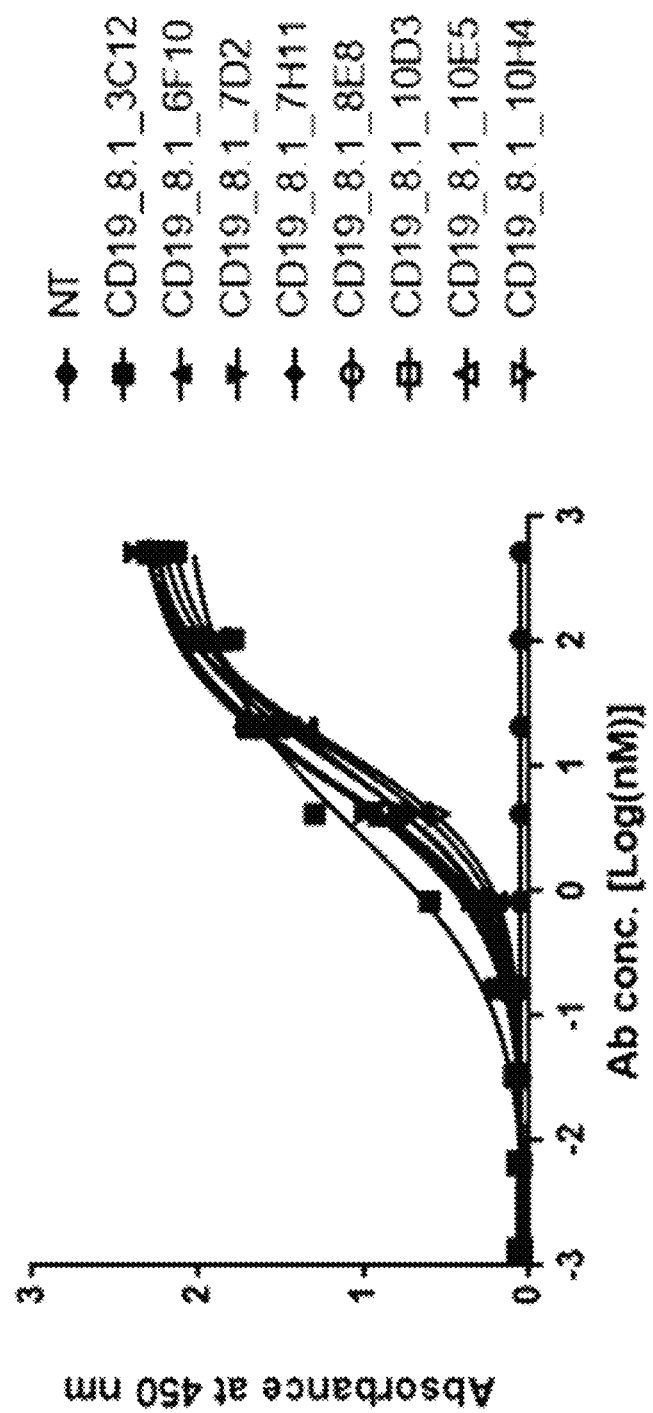
FIG. 7 shows the results of analyzing, through ELISA, the binding of 8 types of affinity-matured antibodies to CD19-ECD Fc protein.

The developed antibody fragments were produced in the form of kappa light chain fusion protein by using FreeStyle™ 293F cell line, and the binding ability to CD19-ECD-Fc was examined by the same method as in Example 2 (FIG. 7), and the Graphpad Prism was performed for binding ability (Table 6).

TABLE 6

Binding ability of affinity-matured antibodies to CD19-ECD Fc ($EC_{50}$)

| Antibody | $EC_{50}$ (nM) |
| --- | --- |
| CD19_8.1_3C12 | 2.99 |
| CD19_8.1_6F10 | 14.22 |
| CD19_8.1_7D2 | 7.68 |
| CD19_8.1_7H11 | 10.49 |
| CD19_8.1_8E8 | 9.75 |
| CD19_8.1_10D3 | 6.98 |
| CD19_8.1_10E5 | 7.01 |
| CD19_8.1_10H4 | 13.88 |

Figure 8:
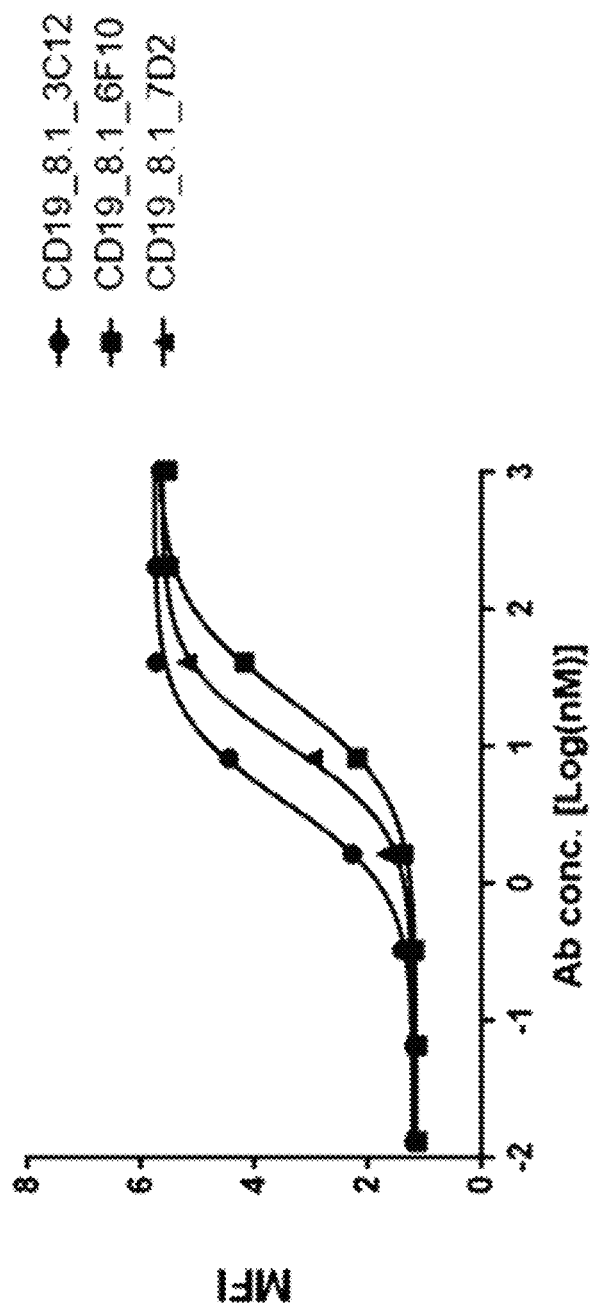
FIG. 8 shows the results of analyzing, through flow cytometry, the binding ability of three types of affinity-matured antibodies to the CD19-positive RaJi cell line.

The ability of the affinity-matured antibody fragments to bind the CD19-positive RaJi cell line was investigated by flow cytometry. The CD19-positive RaJi cell line was treated with the purified antibody fragments in a dose-dependent manner, and the bound antibody fragments were stained with anti-human kappa light chain-FITC (BD bioscience, USA). Out of the antibody fragments binding to the RaJi cell line, three types of antibodies with excellent cell binding ability were analyzed by flow cytometry (FIG. 8), and the Graphpad Prism was performed for binding ability (Table 7). Through this, antibodies with enhanced binding ability compared with CD19_8.1 were secured.

TABLE 7

Binding ability of three types of affinity-matured antibody fragments in RaJi cell line ($EC_{50}$)

| Antibody | $EC_{50}$ (nM) |
| --- | --- |
| CD19_8.1_3C12 | 3.89 |
| CD19_8.1_6F10 | 22.21 |
| CD19_8.1_7D2 | 10.02 |

Example 7: Preparation of Lentivirus Containing Affinity-Matured Antibody Fragment-Linked Chimeric Antigen Receptor Out of the developed antibodies, affinity-matured CD19_8.1_3C12 was used to develop a chimeric antigen receptor. For the chimeric antigen receptor, codon optimization was made of a CD8 leader, an scFv type of developed antibody, hinge and transmembrane domains of CD8, a cytoplasmic domain of CD137, and a cytoplasmic domain of CD3 zeta by using GeneOptimizer (Invitrogen) algorithm. Thereafter, the optimized sequences were digested with SpeI/PacI and ligated to pLenti6.3/V5-TOPO lentiviral vector (Invitrogen, USA) in which the promoter had been modified into EF-1 alpha. The construct thus obtained was sequenced.

The prepared lentiviral construct was transduced, together with the plasmid pCMV-dR8.91 carrying a nucleic acid encoding the vesicular stomatitis Indiana virus G protein (VSV-G), which is a viral coat protein, and the gag, pol, and rev genes, into Lenti-X 293T cells (Takara Bio Inc., Japan). Transduction was performed using Lipofectamine 2000 (Invitrogen, USA) according to the manufacturer's protocol. The cell culture containing lentivirus were enriched with Lenti-X concentrator (Takara Bio Inc., Japan) and stored.

Example 8: Preparation of Cytotoxic T Cells Having Affinity-Matured Antibody Fragment-Bearing Chimeric Antigen Receptor Presented on Surface Thereof, and Verification on Activity Thereof Cytotoxic T cells having CD19_8.1_3C12 antibody fragment (scFv)-bearing chimeric antigen receptor presented on the surface thereof were prepared using the lentivirus prepared in Example 7. The cytotoxic T cells having the chimeric antigen receptor presented on the surface thereof were used to investigate whether the T cells induce the activation of the chimeric antigen receptor by recognizing CD19 on cell surfaces.

Specifically, the lentivirus was transduced into the CD19-positive cell line RaJi such that GFP-Luciferase was expressed, thereby constructing the RaJi-Luc cell line, which is a gene-induced cell line, and the RaJi-Luc cell line was then used in experiments. First, the RaJi-Luc cell line was seeded at a density of $3\times10^4$ cells/well into round-bottom 96-well plates. To the RaJi-Luc cell line-seeded plates, the prepared cytotoxic T cells were added according to a treatment ration per well, followed by incubation together at 37° C. for 24 hours in a 5% $CO_2$ atmosphere. After the incubation, the amount of interferon gamma secreted in the medium was measured using an ELISA kit according to the manufacturer's protocol. The cytotoxic effect of the cytotoxic T cells was identified through luciferase measurement (Bio-Glo Luciferase assay system, Promega, USA).

Figure 9:
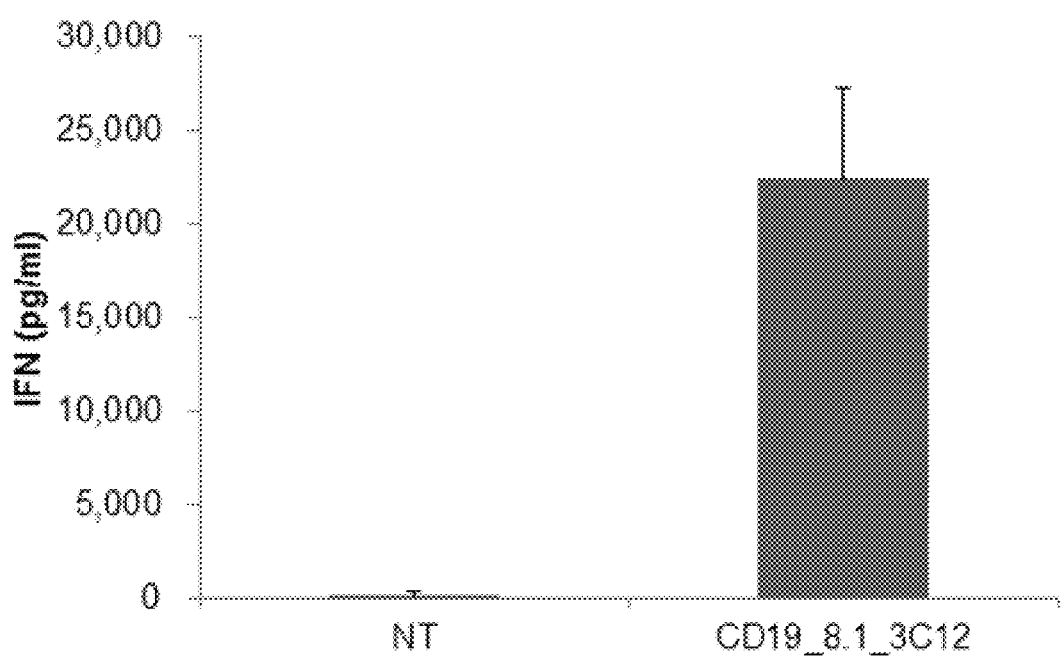
FIG. 9 shows the results of confirming, through the amount of interferon gamma, the activity of cytotoxic T cells expressing the chimeric antigen receptor of CD19_8.1_3C12. The CD19-positive RaJi cells and the CD19-negative Jurkat cells were used as target cells, and each co-incubated with cytotoxic T cells at a ratio of 1:5, and then interferon gamma was measured.
Figure 10:
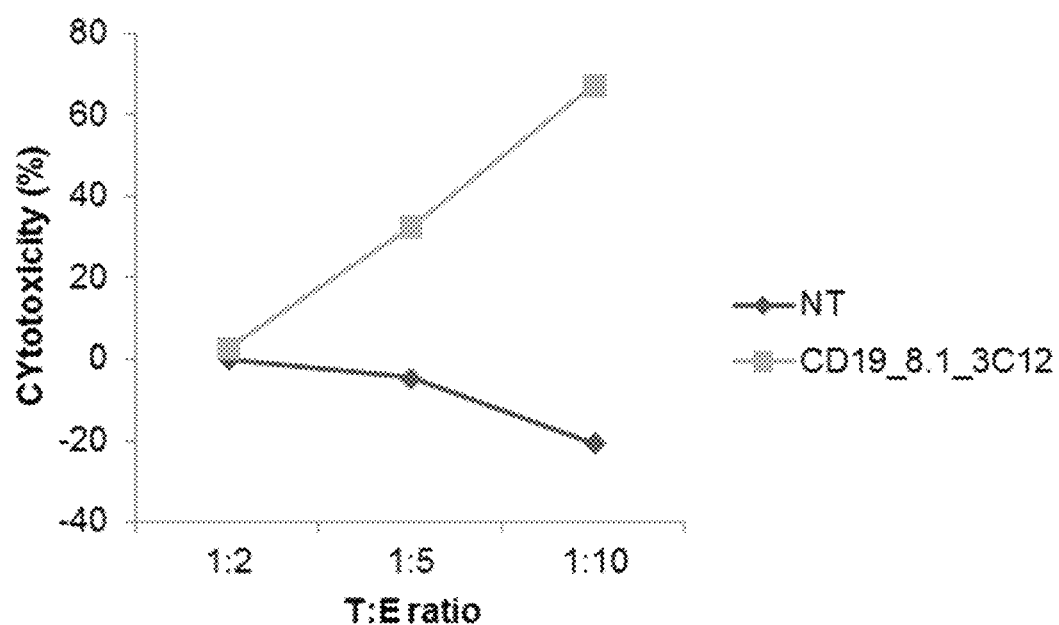
FIG. 10 shows the results of confirming cytotoxicity by measuring luciferase of RaJi-Luc cells surviving after the co-incubation of RaJi-Luc cells, which are a CD19-positive cell line, and cytotoxic T cells.

As can be seen in FIG. 9, significant increases in the secretion of interferon gamma were detected in the experimental group treated with cytotoxic T cells bearing the antibody fragment of the present disclosure and the RaJi-Luc cells at a ratio of 1:5. The cytotoxic effect of the chimeric antigen receptor bearing the antibody fragment of the present disclosure was examined by reacting luciferase with a substrate, the luciferase being eluted from the lysis of the RaJi-Luc cell line remaining after the incubation of the cytotoxic T cells and RaJi-Luc with 3×lysis buffer (75 mM Tris(pH 8.0), 30% glycerol, 3% Triton X100). The percentage of lysis was determined on the basis of 100% of the signal detected in the well where only Raji-Luc cells were cultured. It was verified that the chimeric antigen receptor T cells having the antibody fragment of the present disclosure showed the cytotoxic effect depending on the treatment ratio (FIG. 10).

This application contains references to amino acid sequences and/or nucleic acid sequences which have been submitted herewith as the sequence listing text file entitled "000214_Seq_List.TXT", file size 138 KiloBytes (KB), created on 3 Mar. 2022. The aforementioned sequence listing is hereby incorporated by reference in its entirety pursuant to 37 C.F.R. § 1.52(e).

What is claimed is:

1. An anti-CD19 antibody or an antigen-binding fragment thereof, comprising:
    a heavy chain variable region (VH) comprising a CDRH1 of SEQ ID NO: 1, a CDRH2, and a CDRH3 of SEQ ID NO: 3; and a light chain variable region (VL) comprising a CDRL1, a CDRL2 of SEQ ID NO: 5, and a CDRL3 of SEQ ID NO: 6,
    wherein the CDRH2 and CDRL1, respectively, comprise the amino acid sequences of SEQ ID NOS: 2 and 4, SEQ ID NOS: 7 and 49, SEQ ID NOS: 8 and 50, SEQ ID NOS: 9 and 51, SEQ ID NOS: 10 and 52, SEQ ID NOS: 11 and 53, SEQ ID NOS: 12 and 54, SEQ ID NOS: 13 and 55, SEQ ID NOS: 14 and 56, SEQ ID NOS: 15 and 57, SEQ ID NOS: 16 and 58, SEQ ID NOS: 17 and 59, SEQ ID NOS: 18 and 60, SEQ ID NOS: 19 and 61, SEQ ID NOS: 20 and 62, SEQ ID NOS: 21 and 63, SEQ ID NOS: 22 and 64, SEQ ID NOS: 23 and 65, SEQ ID NOS: 24 and 66, SEQ ID NOS: 25 and 67, SEQ ID NOS: 26 and 68, SEQ ID NOS: 27 and 69, SEQ ID NOS: 28 and 70, SEQ ID NOS: 29 and 71, SEQ ID NOS: 30 and 72, SEQ ID NOS: 31 and 73, SEQ ID NOS: 32 and 74, SEQ ID NOS: 33 and 75, SEQ ID NOS: 34 and 76, SEQ ID NOS: 35 and 77, SEQ ID NOS: 36 and 78, SEQ ID NOS: 37 and 79, SEQ ID NOS: 38 and 80, SEQ ID NOS: 39 and 81, SEQ ID NOS: 40 and 82, SEQ ID NOS: 41 and 83, SEQ ID NOS: 42 and 84, SEQ ID NOS: 43 and 85, SEQ ID NOS: 44 and 86, SEQ ID NOS: 45 and 87, SEQ ID NOS: 46 and 88, SEQ ID NOS: 47 and 89, or SEQ ID NOS: 48 and 90.

2. The anti-CD19 antibody or the antigen-binding fragment thereof of claim 1, wherein the heavy chain variable region (VH) comprises an amino acid sequence selected from the group consisting of SEQ ID NOS: 91-133.

3. The anti-CD19 antibody or the antigen-binding fragment thereof of claim 1, wherein the light chain variable region (VL) comprises an amino acid sequence selected from the group consisting of SEQ ID NOS: 134-176.

4. The anti-CD19 antibody or the antigen-binding fragment thereof of claim 1, wherein the heavy chain variable region (VH) and the light chain variable region (VL), respectively, comprise the amino acid sequences of SEQ ID NOS: 91 and 134, SEQ ID NOS: 92 and 135, SEQ ID NOS: 93 and 136, SEQ ID NOS: 94 and 137, SEQ ID NOS: 95 and 138, SEQ ID NOS: 96 and 139, SEQ ID NOS: 97 and 140, SEQ ID NOS: 98 and 141, SEQ ID NOS: 99 and 142, SEQ ID NOS: 100 and 143, SEQ ID NOS: 101 and 144, SEQ ID NOS: 102 and 145, SEQ ID NOS: 103 and 146, SEQ ID NOS: 104 and 147, SEQ ID NOS: 105 and 148, SEQ ID NOS: 106 and 149, SEQ ID NOS: 107 and 150, SEQ ID NOS: 108 and 151, SEQ ID NOS: 109 and 152, SEQ ID NOS: 110 and 153, SEQ ID NOS: 111 and 154, SEQ ID NOS: 112 and 155, SEQ ID NOS: 113 and 156, SEQ ID NOS: 114 and 157, SEQ ID NOS: 115 and 158, SEQ ID NOS: 116 and 159, SEQ ID NOS: 117 and 160, SEQ ID NOS: 118 and 161, SEQ ID NOS: 119 and 162, SEQ ID NOS: 120 and 163, SEQ ID NOS: 121 and 164, SEQ ID NOS: 122 and 165, SEQ ID NOS: 123 and 166, SEQ ID NOS: 124 and 167, SEQ ID NOS: 125 and 168, SEQ ID NOS: 126 and 169, SEQ ID NOS: 127 and 170, SEQ ID NOS: 128 and 171, SEQ ID NOS: 129 and 172, SEQ ID NOS: 130 and 173, SEQ ID NOS: 131 and 174, SEQ ID NOS: 132 and 175, or SEQ ID NOS: 133 and 176.

5. An anti-CD19 antibody or an antigen-binding fragment thereof comprising:
    a heavy chain variable region (VH) comprising a CDRH1 of SEQ ID NO: 1, a CDRH2, and a CDRH3; and a light chain variable region (VL) comprising a CDRL1, a CDRL2 of SEQ ID NO: 5, and a CDRL3 of SEQ ID NO: 6,
    wherein the CDRH2, CDRH3, and CDRL1, respectively, comprise the amino acid sequences of SEQ ID NOS: 190, 191, and 199; SEQ ID NOS: 190, 192, and 199; SEQ ID NOS: 190, 193, and 199; SEQ ID NOS: 190, 194, and 199; SEQ ID NOS: 190, 195, and 199; SEQ ID NOS: 190, 196, and 200; SEQ ID NOS: 190, 197, and 199; or SEQ ID NOS: 190, 198, and 199.

6. A CD19-specific chimeric antigen receptor, comprising:
    (a) an extracellular domain comprising the anti-CD19 antibody or the antigen-binding fragment thereof of claim 1;
    (b) a transmembrane domain; and
    (c) an intracellular signaling domain.

7. A pharmaceutical composition comprising an effector cell expressing the chimeric antigen receptor of claim 6.

8. A CD19-specific chimeric antigen receptor comprising:
    (a) an extracellular domain comprising the anti-CD19 antibody or the antigen-binding fragment thereof of claim 5;
    (b) a transmembrane domain; and
    (c) an intracellular signaling domain.

9. A pharmaceutical composition comprising an effector cell expressing the chimeric antigen receptor of claim 8.

* * * * *

SEQUENCE LISTING

```
<160> NUMBER OF SEQ ID NOS: 204

<210> SEQ ID NO 1
<211> LENGTH: 5
<212> TYPE: PRT
<213> ORGANISM: Artificial Sequence
<220> FEATURE:
<223> OTHER INFORMATION: Amino acid sequence of CDRH1 of CD19_8.1
      antibody

<400> SEQUENCE: 1

Asp Tyr Tyr Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Amino acid sequence of CDRH2 of CD19_8.1
      antibody

<400> SEQUENCE: 2

Gly Ile Tyr Tyr Asp Asp Ser Ser Gln Tyr Tyr Ala Asp Ser Val Lys
1               5                   10                  15

Gly

<210> SEQ ID NO 3
<211> LENGTH: 18
<212> TYPE: PRT
<213> ORGANISM: Artificial Sequence
<220> FEATURE:
<223> OTHER INFORMATION: Amino acid sequence of CDRH3 of CD19_8.1
      antibody

<400> SEQUENCE: 3

Gly Pro Leu Phe Cys Asn Asp Arg Thr Cys Ser Tyr Tyr Ala Met
1               5                   10                  15

Asp Val

<210> SEQ ID NO 4
<211> LENGTH: 13
<212> TYPE: PRT
<213> ORGANISM: Artificial Sequence
<220> FEATURE:
<223> OTHER INFORMATION: Amino acid sequence of CDRL1 of CD19_8.1
      antibody
```

```
<400> SEQUENCE: 4

Thr Gly Ser Ser Ser Asn Ile Gly Ser Asn Ala Val Tyr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Amino acid sequence of CDRL2 of CD19_8.1
      antibody

<400> SEQUENCE: 5

Asp Asp Asn His Arg Pro Ser
1               5

<210> SEQ ID NO 6
<211> LENGTH: 11
<212> TYPE: PRT
<213> ORGANISM: Artificial Sequence
<220> FEATURE:
<223> OTHER INFORMATION: Amino acid sequence of CDRL3 of CD19_8.1
      antibody

<400> SEQUENCE: 6

Gly Thr Trp Asp Tyr Ser Leu Ser Gly Tyr Val
1               5                   10

<210> SEQ ID NO 7
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone 2B1

<400> SEQUENCE: 7

Gly Ile Tyr Tyr Asp Gly Ser Ala Arg Tyr Tyr Ala Asp Ser Val Lys
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone B12

<400> SEQUENCE: 8

Gly Ile Tyr Tyr Asp Gly Ser Ala Lys Tyr Tyr Ala Asp Ser Val Lys
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone T2H3

<400> SEQUENCE: 9

Gly Ile Tyr Tyr Asp Gly Ser Ala Lys Tyr Tyr Ala Asp Ser Val Lys
1               5                   10                  15
```

Gly

<210> SEQ ID NO 10
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone T3C1

<400> SEQUENCE: 10

Gly Ile Tyr Tyr Asp Gly Ser Ala Ser Tyr Tyr Ala Asp Ser Val Lys
1               5                   10                  15
Gly

<210> SEQ ID NO 11
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone D10

<400> SEQUENCE: 11

Gly Ile Tyr Tyr Asp Gly Ser Ala Val Tyr Tyr Ala Asp Ser Val Lys
1               5                   10                  15
Gly

<210> SEQ ID NO 12
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone F6

<400> SEQUENCE: 12

Gly Ile Tyr Tyr Asp Gly Ser Ala Lys Tyr Tyr Ala Asp Ser Val Lys
1               5                   10                  15
Gly

<210> SEQ ID NO 13
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone B2

<400> SEQUENCE: 13

Gly Ile Tyr Tyr Asp Gly Ser Thr Lys Tyr Tyr Ala Asp Ser Val Lys
1               5                   10                  15
Gly

<210> SEQ ID NO 14
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone B6

<400> SEQUENCE: 14

Gly Ile Tyr Tyr Asp Gly Ser Thr Ala Tyr Tyr Ala Asp Ser Val Lys

<210> SEQ ID NO 15
<211> LENGTH: 17
<212> TYPE: PRT
<213> ORGANISM: Artificial Sequence
<220> FEATURE:
<223> OTHER INFORMATION: Amino acid sequence of CDRH2 of affinity matured clone 2F1

<400> SEQUENCE: 15

Gly Ile Tyr Tyr Asp Gly Ser Ser Gln Gly Trp Ser Ser Val Lys
1               5                   10                  15
Gly

<210> SEQ ID NO 16
<211> LENGTH: 17
<212> TYPE: PRT
<213> ORGANISM: Artificial Sequence
<220> FEATURE:
<223> OTHER INFORMATION: Amino acid sequence of CDRH2 of affinity matured clone C8

<400> SEQUENCE: 16

Gly Ile Tyr Tyr Asp Gly Ser Gln Leu Tyr Tyr Ala Asp Ser Val Lys
1               5                   10                  15
Gly

<210> SEQ ID NO 17
<211> LENGTH: 17
<212> TYPE: PRT
<213> ORGANISM: Artificial Sequence
<220> FEATURE:
<223> OTHER INFORMATION: Amino acid sequence of CDRH2 of affinity matured clone D4

<400> SEQUENCE: 17

Gly Ile Tyr Tyr Asp Gly Ser Ser Gln Ser Met Ala Gly Ser Val Lys
1               5                   10                  15
Gly

<210> SEQ ID NO 18
<211> LENGTH: 17
<212> TYPE: PRT
<213> ORGANISM: Artificial Sequence
<220> FEATURE:
<223> OTHER INFORMATION: Amino acid sequence of CDRH2 of affinity matured clone B5

<400> SEQUENCE: 18

Gly Ile Tyr Tyr Asp Gly Ser Ser Gln Gly Met Thr Asn Ser Val Lys
1               5                   10                  15
Gly

<210> SEQ ID NO 19
<211> LENGTH: 17
<212> TYPE: PRT
<213> ORGANISM: Artificial Sequence
<220> FEATURE:
<223> OTHER INFORMATION: Amino acid sequence of CDRH2 of affinity matured clone G4

<400> SEQUENCE: 19

```
Gly Ile Tyr Tyr Asp Gly Ser Ser Gln Thr Leu Leu Pro Ser Val Lys
1               5                   10                  15

Gly
```

<210> SEQ ID NO 20
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone A7

<400> SEQUENCE: 20

```
Gly Ile Tyr Tyr Asp Ala Ser Trp Thr Tyr Tyr Ala Asp Ser Val Lys
1               5                   10                  15

Gly
```

<210> SEQ ID NO 21
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone D12

<400> SEQUENCE: 21

```
Gly Ile Tyr Tyr Asp Ala Ser Thr Lys Tyr Tyr Ala Asp Ser Val Lys
1               5                   10                  15

Gly
```

<210> SEQ ID NO 22
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone E2

<400> SEQUENCE: 22

```
Gly Ile Tyr Tyr Asp Ala Ser Ile Arg Tyr Tyr Ala Asp Ser Val Lys
1               5                   10                  15

Gly
```

<210> SEQ ID NO 23
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone T2A1

<400> SEQUENCE: 23

```
Gly Ile Tyr Tyr Asp Ala Ser Val Lys Tyr Tyr Ala Asp Ser Val Lys
1               5                   10                  15

Gly
```

<210> SEQ ID NO 24
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone T3H9

<400> SEQUENCE: 24

Gly Ile Tyr Tyr Asp Ala Ser Ala Glu Tyr Tyr Ala Asp Ser Val Lys
1               5                   10                  15

Gly

<210> SEQ ID NO 25
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone 2G1

<400> SEQUENCE: 25

Gly Ile Tyr Tyr Asp Ser Ser Thr Arg Tyr Tyr Ala Asp Ser Val Lys
1               5                   10                  15

Gly

<210> SEQ ID NO 26
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone C4

<400> SEQUENCE: 26

Gly Ile Tyr Tyr Asp Ser Ser Met Arg Tyr Tyr Ala Asp Ser Val Lys
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone C5

<400> SEQUENCE: 27

Gly Ile Tyr Tyr Asp Ser Ser Met Arg Tyr Tyr Ala Asp Ser Val Lys
1               5                   10                  15

Gly

<210> SEQ ID NO 28
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone D1

<400> SEQUENCE: 28

Gly Ile Tyr Tyr Asp Ser Ser Ala Lys Tyr Tyr Ala Asp Ser Val Lys
1               5                   10                  15

Gly

<210> SEQ ID NO 29
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone D2

```
<400> SEQUENCE: 29

Gly Ile Tyr Tyr Asp Ser Ser Thr Asp Tyr Tyr Ala Asp Ser Val Lys
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone E1

<400> SEQUENCE: 30

Gly Ile Tyr Tyr Asp Ser Ser Val Thr Tyr Tyr Ala Asp Ser Val Lys
1               5                   10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone F3

<400> SEQUENCE: 31

Gly Ile Tyr Tyr Asp Ser Ser Ala Arg Tyr Tyr Ala Asp Ser Val Lys
1               5                   10                  15

Gly

<210> SEQ ID NO 32
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone T2C1

<400> SEQUENCE: 32

Gly Ile Tyr Tyr Asp Ser Ser Gln Asp Tyr Tyr Ala Asp Ser Val Lys
1               5                   10                  15

Gly

<210> SEQ ID NO 33
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone T2H1

<400> SEQUENCE: 33

Gly Ile Tyr Tyr Asp Ser Ser Gln Asp Tyr Tyr Ala Asp Ser Val Lys
1               5                   10                  15

Gly

<210> SEQ ID NO 34
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone T2H5
```

```
<400> SEQUENCE: 34

Gly Ile Tyr Tyr Asp Ser Ser Ala Lys Tyr Tyr Ala Asp Ser Val Lys
1               5                   10                  15

Gly

<210> SEQ ID NO 35
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone T3B8

<400> SEQUENCE: 35

Gly Ile Tyr Tyr Asp Ser Ser Val Met Tyr Tyr Ala Asp Ser Val Lys
1               5                   10                  15

Gly

<210> SEQ ID NO 36
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone A12

<400> SEQUENCE: 36

Gly Ile Tyr Tyr Asp Gly Thr Val Leu Tyr Tyr Ala Asp Ser Val Lys
1               5                   10                  15

Gly

<210> SEQ ID NO 37
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone C2

<400> SEQUENCE: 37

Gly Ile Tyr Tyr Asp Gly Thr Asn Gln Tyr Tyr Ala Asp Ser Val Lys
1               5                   10                  15

Gly

<210> SEQ ID NO 38
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone D7

<400> SEQUENCE: 38

Gly Ile Tyr Tyr Asp Gly Thr Ala Phe Tyr Tyr Ala Asp Ser Val Lys
1               5                   10                  15

Gly

<210> SEQ ID NO 39
<211> LENGTH: 17
<212> TYPE: PRT
<213> ORGANISM: Artificial Sequence
<220> FEATURE:
<223> OTHER INFORMATION: Amino acid sequence of CDRH2 of affinity
``` matured clone E3

<400> SEQUENCE: 39

Gly Ile Tyr Tyr Asp Gly Thr Ala Met Tyr Tyr Ala Asp Ser Val Lys
1               5                   10                  15

Gly

<210> SEQ ID NO 40
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone H10

<400> SEQUENCE: 40

Gly Ile Tyr Tyr Asp Gly Thr Asn Val Tyr Tyr Ala Asp Ser Val Lys
1               5                   10                  15

Gly

<210> SEQ ID NO 41
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone T3F5

<400> SEQUENCE: 41

Gly Ile Tyr Tyr Asp Gly Thr Ala Lys Tyr Tyr Ala Asp Ser Val Lys
1               5                   10                  15

Gly

<210> SEQ ID NO 42
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone A10

<400> SEQUENCE: 42

Gly Ile Tyr Tyr Asp Gly Ile Tyr Arg Tyr Tyr Ala Asp Ser Val Lys
1               5                   10                  15

Gly

<210> SEQ ID NO 43
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone T3H1

<400> SEQUENCE: 43

Gly Ile Tyr Tyr Asp Gly Ala Val Gln Tyr Tyr Ala Asp Ser Val Lys
1               5                   10                  15

Gly

<210> SEQ ID NO 44
<211> LENGTH: 17
<212> TYPE: PRT
<213> ORGANISM: Artificial Sequence
<220> FEATURE:

```
<223> OTHER INFORMATION: Amino acid sequence of CDRH2 of affinity
      matured clone B1

<400> SEQUENCE: 44

Gly Ile Tyr Tyr Asp Gly Asp Val Arg Tyr Tyr Ala Asp Ser Val Lys
1               5                   10                  15
Gly

<210> SEQ ID NO 45
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone B7

<400> SEQUENCE: 45

Gly Ile Tyr Tyr Asp Gly Phe Ala Pro Tyr Tyr Ala Asp Ser Val Lys
1               5                   10                  15
Gly

<210> SEQ ID NO 46
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone D8

<400> SEQUENCE: 46

Gly Ile Tyr Tyr Asp Gly Leu His Gln Tyr Tyr Ala Asp Ser Val Lys
1               5                   10                  15
Gly

<210> SEQ ID NO 47
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone E12

<400> SEQUENCE: 47

Gly Ile Tyr Tyr Asp Ser Phe Val Pro Tyr Tyr Ala Asp Ser Val Lys
1               5                   10                  15
Gly

<210> SEQ ID NO 48
<211> LENGTH: 17
<212> TYPE: PRT
<213> ORGANISM: Artificial Sequence
<220> FEATURE:
<223> OTHER INFORMATION: Amino acid sequence of CDRH2 of affinity
      matured clone T2A12

<400> SEQUENCE: 48

Gly Ile Tyr Tyr Asp Gly His Gln Gln Tyr Tyr Ala Asp Ser Val Lys
1               5                   10                  15
Gly

<210> SEQ ID NO 49
<211> LENGTH: 13
<212> TYPE: PRT
<213> ORGANISM: Artificial Sequence
```

```
<220> FEATURE:
<223> OTHER INFORMATION: Amino acid sequence of CDRL1 of affinity
      matured clone 2B1

<400> SEQUENCE: 49

Val Gly Gly Val Ser Asn Ile Gly Ser Asn Ala Val Tyr
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone B12

<400> SEQUENCE: 50

Ala Gly His Tyr Ser Asn Ile Gly Ser Asn Ala Val Tyr
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone T2H3

<400> SEQUENCE: 51

Gly Gly Gly Ile Ser Asn Ile Gly Ser Asn Ala Val Tyr
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone T3C1

<400> SEQUENCE: 52

Ser Gly Gly Pro Ser Asn Ile Gly Ser Asn Ala Val Tyr
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone D10

<400> SEQUENCE: 53

Trp Gly Asp Tyr Ser Asn Ile Gly Ser Asn Ala Val Tyr
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone F6

<400> SEQUENCE: 54

Trp Gly Leu Pro Ser Asn Ile Gly Ser Asn Ala Val Tyr
1               5                   10
```

```
<210> SEQ ID NO 55
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone B2

<400> SEQUENCE: 55

Ala Gly Gly Val Ser Asn Ile Gly Ser Asn Ala Val Tyr
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone B6

<400> SEQUENCE: 56

Asn Gly Thr Pro Ser Asn Ile Gly Ser Asn Ala Val Tyr
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone 2F1

<400> SEQUENCE: 57

Tyr Gly Gln Pro Ser Asn Ile Gly Ser Asn Ala Val Tyr
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone C8

<400> SEQUENCE: 58

Lys Gly Gly Met Ser Asn Ile Gly Ser Asn Ala Val Tyr
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone D4

<400> SEQUENCE: 59

Thr Gly Gly Val Ser Asn Ile Gly Ser Asn Ala Val Tyr
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone B5
```

```
<400> SEQUENCE: 60

His Gly Thr Pro Ser Asn Ile Gly Ser Asn Ala Val Tyr
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone G4

<400> SEQUENCE: 61

Val Gly Lys Pro Ser Asn Ile Gly Ser Asn Ala Val Tyr
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone A7

<400> SEQUENCE: 62

Thr Gly Asn Pro Ser Asn Ile Gly Ser Asn Ala Val Tyr
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone D12

<400> SEQUENCE: 63

Arg Gly Ser Ala Ser Asn Ile Gly Ser Asn Ala Val Tyr
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone E2

<400> SEQUENCE: 64

Lys Gly Met Ile Ser Asn Ile Gly Ser Asn Ala Val Tyr
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone T2A1

<400> SEQUENCE: 65

Ala Gly Lys Pro Ser Asn Ile Gly Ser Asn Ala Val Tyr
1               5                   10

<210> SEQ ID NO 66
<211> LENGTH: 13
<212> TYPE: PRT
```

<213> ORGANISM: Artificial Sequence
<220> FEATURE:
<223> OTHER INFORMATION: Amino acid sequence of CDRL1 of affinity
      matured clone T3H9

<400> SEQUENCE: 66

Ser Gly Met Leu Ser Asn Ile Gly Ser Asn Ala Val Tyr
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone 2G1

<400> SEQUENCE: 67

Lys Gly Ser Phe Ser Asn Ile Gly Ser Asn Ala Val Tyr
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone C4

<400> SEQUENCE: 68

Gly Gly Gln Pro Ser Asn Ile Gly Ser Asn Ala Val Tyr
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone C5

<400> SEQUENCE: 69

Lys Gly Gly Met Ser Asn Ile Gly Ser Asn Ala Val Tyr
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone D1

<400> SEQUENCE: 70

Ser Gly Gly Pro Ser Asn Ile Gly Ser Asn Ala Val Tyr
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone D2

<400> SEQUENCE: 71

Gln Gly Gln Pro Ser Asn Ile Gly Ser Asn Ala Val Tyr
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone E1

<400> SEQUENCE: 72

Thr Gly Asn Pro Ser Asn Ile Gly Ser Asn Ala Val Tyr
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone F3

<400> SEQUENCE: 73

Thr Gly Ser Ser Ser Asn Ile Gly Ser Ala Pro Leu Tyr
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone T2C1

<400> SEQUENCE: 74

Arg Gly Gly Pro Ser Asn Ile Gly Ser Asn Ala Val Tyr
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone T2H1

<400> SEQUENCE: 75

Gln Gly Gly Tyr Ser Asn Ile Gly Ser Asn Ala Val Tyr
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone T2H5

<400> SEQUENCE: 76

Ser Gly Asn Pro Ser Asn Ile Gly Ser Asn Ala Val Tyr
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone T3B8

<400> SEQUENCE: 77

Glu Gly Ser Pro Ser Asn Ile Gly Ser Asn Ala Val Tyr
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone A12

<400> SEQUENCE: 78

Gln Gly Gly Pro Ser Asn Ile Gly Ser Asn Ala Val Tyr
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone C2

<400> SEQUENCE: 79

Thr Gly Gly Leu Ser Asn Ile Gly Ser Asn Ala Val Tyr
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone D7

<400> SEQUENCE: 80

Glu Gly Gln Pro Ser Asn Ile Gly Ser Asn Ala Val Tyr
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone E3

<400> SEQUENCE: 81

Ser Gly Gly Tyr Ser Asn Ile Gly Ser Asn Ala Val Tyr
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone H10

<400> SEQUENCE: 82

Leu Gly Gly Tyr Ser Asn Ile Gly Ser Asn Ala Val Tyr
1               5                   10

<210> SEQ ID NO 83
<211> LENGTH: 13

<212> TYPE: PRT
<213> ORGANISM: Artificial Sequence
<220> FEATURE:
<223> OTHER INFORMATION: Amino acid sequence of CDRL1 of affinity
      matured clone T3F5

<400> SEQUENCE: 83

His Gly Gln Pro Ser Asn Ile Gly Ser Asn Ala Val Tyr
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone A10

<400> SEQUENCE: 84

Ser Gly Asp Pro Ser Asn Ile Gly Ser Asn Ala Val Tyr
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone T3H1

<400> SEQUENCE: 85

Asp Gly Gly Tyr Ser Asn Ile Gly Ser Asn Ala Val Tyr
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone B1

<400> SEQUENCE: 86

Val Gly Ser Pro Ser Asn Ile Gly Ser Asn Ala Val Tyr
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone B7

<400> SEQUENCE: 87

Arg Gly Thr Pro Ser Asn Ile Gly Ser Asn Ala Val Tyr
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Amino acid sequence of CDRL1 of affinity
      matured clone D8

<400> SEQUENCE: 88

Val Gly Asn Leu Ser Asn Ile Gly Ser Asn Ala Val Tyr

<210> SEQ ID NO 89
<211> LENGTH: 13
<212> TYPE: PRT
<213> ORGANISM: Artificial Sequence
<220> FEATURE:
<223> OTHER INFORMATION: Amino acid sequence of CDRL1 of affinity matured clone E12

<400> SEQUENCE: 89

Ala Gly Ser Ala Ser Asn Ile Gly Ser Asn Ala Val Tyr
1               5                   10

<210> SEQ ID NO 90
<211> LENGTH: 13
<212> TYPE: PRT
<213> ORGANISM: Artificial Sequence
<220> FEATURE:
<223> OTHER INFORMATION: Amino acid sequence of CDRL1 of affinity matured clone T2A12

<400> SEQUENCE: 90

Thr Gly Ser Ser Ser Asn Ile Gly Ser Ala Pro Thr Tyr
1               5                   10

<210> SEQ ID NO 91
<211> LENGTH: 127
<212> TYPE: PRT
<213> ORGANISM: Artificial Sequence
<220> FEATURE:
<223> OTHER INFORMATION: Amino acid sequence of heavy chain variable region of CD19_8.1 antibody

<400> SEQUENCE: 91

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Asp Ser Ser Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 92
<211> LENGTH: 127
<212> TYPE: PRT
<213> ORGANISM: Artificial Sequence
<220> FEATURE:
<223> OTHER INFORMATION: Amino acid sequence of heavy chain variable region of affinity matured clone 2B1

<400> SEQUENCE: 92

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Ser Ala Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
            115                 120                 125

<210> SEQ ID NO 93
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone B12

<400> SEQUENCE: 93

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Ser Ala Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
            115                 120                 125

<210> SEQ ID NO 94
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone T2H3

<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Ser Ala Lys Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125
```

<210> SEQ ID NO 95
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone T3C1

<400> SEQUENCE: 95

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
             20                  25                  30

Tyr Met Ser Trp Val Arg Gln Ala Pro Gly Lys Gly Leu Glu Trp Val
         35                  40                  45

Ser Gly Ile Tyr Tyr Asp Gly Ser Ala Ser Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125
```

<210> SEQ ID NO 96
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone D10

<400> SEQUENCE: 96

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
             20                  25                  30

Tyr Met Ser Trp Val Arg Gln Ala Pro Gly Lys Gly Leu Glu Trp Val
         35                  40                  45

Ser Gly Ile Tyr Tyr Asp Gly Ser Ala Val Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Pro Leu Phe Cys Asn Asp Arg Thr Cys Ser Tyr Tyr Tyr
            100                 105                 110
```

```
Ala Met Asp Val Trp Gly Gln Gly Thr Leu Val Thr Val Ser Ser
        115                 120                 125
```

<210> SEQ ID NO 97
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone F6

<400> SEQUENCE: 97

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Ser Ala Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125
```

<210> SEQ ID NO 98
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone B2

<400> SEQUENCE: 98

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Ser Thr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125
```

<210> SEQ ID NO 99
<211> LENGTH: 127
<212> TYPE: PRT
<213> ORGANISM: Artificial Sequence
<220> FEATURE:

<223> OTHER INFORMATION: Amino acid sequence of heavy chain variable
      region of affinity matured clone B6

<400> SEQUENCE: 99

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Ser Thr Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 100
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone 2F1

<400> SEQUENCE: 100

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Ser Ser Gln Gly Trp Ser Ser Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 101
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone C8

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr

```
            20                  25                  30
Tyr Met Ser Trp Val Arg Gln Ala Pro Gly Lys Gly Leu Glu Trp Val
            35                  40                  45

Ser Gly Ile Tyr Tyr Asp Gly Ser Gln Leu Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
            115                 120                 125

<210> SEQ ID NO 102
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone D4

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
            35                  40                  45

Ser Gly Ile Tyr Tyr Asp Gly Ser Ser Gln Ser Met Ala Gly Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
            115                 120                 125

<210> SEQ ID NO 103
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone B5

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
            35                  40                  45

Ser Gly Ile Tyr Tyr Asp Gly Ser Ser Gln Gly Met Thr Asn Ser Val
        50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                    85                  90                  95

Ala Lys Gly Pro Leu Phe Cys Asn Asp Arg Thr Cys Ser Tyr Tyr Tyr
                100                 105                 110

Ala Met Asp Val Trp Gly Gln Gly Thr Leu Val Thr Val Ser Ser
            115                 120                 125

<210> SEQ ID NO 104
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone G4

<400> SEQUENCE: 104

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Ser Ser Gln Thr Leu Leu Pro Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Lys Gly Pro Leu Phe Cys Asn Asp Arg Thr Cys Ser Tyr Tyr Tyr
                100                 105                 110

Ala Met Asp Val Trp Gly Gln Gly Thr Leu Val Thr Val Ser Ser
            115                 120                 125

<210> SEQ ID NO 105
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone A7

<400> SEQUENCE: 105

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Ala Ser Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Lys Gly Pro Leu Phe Cys Asn Asp Arg Thr Cys Ser Tyr Tyr Tyr
                100                 105                 110

Ala Met Asp Val Trp Gly Gln Gly Thr Leu Val Thr Val Ser Ser
```

115             120             125

<210> SEQ ID NO 106
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone D12

<400> SEQUENCE: 106

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Ala Ser Thr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 107
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone E2

<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Ala Ser Ile Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 108
<211> LENGTH: 127
<212> TYPE: PRT
<213> ORGANISM: Artificial Sequence
<220> FEATURE:
<223> OTHER INFORMATION: Amino acid sequence of heavy chain variable -continued region of affinity matured clone T2A1

<400> SEQUENCE: 108

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Ala Ser Val Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 109
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone T3H9

<400> SEQUENCE: 109

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Ala Ser Ala Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 110
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone 2G1

<400> SEQUENCE: 110

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

```
Tyr Met Ser Trp Val Arg Gln Ala Pro Gly Lys Gly Leu Glu Trp Val
        35                  40                  45

Ser Gly Ile Tyr Tyr Asp Ser Ser Thr Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
            115                 120                 125

<210> SEQ ID NO 111
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone C4

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Ser Ser Met Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
            115                 120                 125

<210> SEQ ID NO 112
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone C5

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Ser Ser Met Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 113
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone D1

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Ser Ser Ala Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 114
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone D2

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Ser Ser Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125
```

<210> SEQ ID NO 115
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone E1

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Ser Ser Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 116
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone F3

<400> SEQUENCE: 116

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Ser Ser Ala Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 117
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone T2C1

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Ser Ser Gln Asp Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 118
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone T2H1

<400> SEQUENCE: 118

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Ser Ser Gln Asp Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 119
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone T2H5

<400> SEQUENCE: 119

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
            35                  40                  45

Ser Gly Ile Tyr Tyr Asp Ser Ser Ala Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
            115                 120                 125

<210> SEQ ID NO 120
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone T3B8

<400> SEQUENCE: 120

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
            35                  40                  45

Ser Gly Ile Tyr Tyr Asp Ser Ser Val Met Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
            115                 120                 125

<210> SEQ ID NO 121
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone A12

<400> SEQUENCE: 121

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
            35                  40                  45

Ser Gly Ile Tyr Tyr Asp Gly Thr Val Leu Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

```
Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 122
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone C2

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Thr Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 123
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone D7

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Thr Ala Phe Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125
```

<210> SEQ ID NO 124
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone E3

<400> SEQUENCE: 124

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Thr Ala Met Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 125
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone H10

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Thr Asn Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 126
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone T3F5

<400> SEQUENCE: 126

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Thr Ala Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 127
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone A10

<400> SEQUENCE: 127

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Ile Tyr Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 128
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone T3H1

<400> SEQUENCE: 128

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val

```
                35                  40                  45
Ser Gly Ile Tyr Tyr Asp Gly Ala Val Gln Tyr Tyr Ala Asp Ser Val
             50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Pro Leu Phe Cys Asn Asp Arg Thr Cys Ser Tyr Tyr Tyr
                100                 105                 110

Ala Met Asp Val Trp Gly Gln Gly Thr Leu Val Thr Val Ser Ser
            115                 120                 125

<210> SEQ ID NO 129
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone B1

<400> SEQUENCE: 129

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
             20                  25                  30

Tyr Met Ser Trp Val Arg Gln Ala Pro Gly Lys Gly Leu Glu Trp Val
         35                  40                  45

Ser Gly Ile Tyr Tyr Asp Gly Asp Val Arg Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Pro Leu Phe Cys Asn Asp Arg Thr Cys Ser Tyr Tyr Tyr
                100                 105                 110

Ala Met Asp Val Trp Gly Gln Gly Thr Leu Val Thr Val Ser Ser
            115                 120                 125

<210> SEQ ID NO 130
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone B7

<400> SEQUENCE: 130

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
             20                  25                  30

Tyr Met Ser Trp Val Arg Gln Ala Pro Gly Lys Gly Leu Glu Trp Val
         35                  40                  45

Ser Gly Ile Tyr Tyr Asp Gly Phe Ala Pro Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

```
                    85                  90                  95

Ala Lys Gly Pro Leu Phe Cys Asn Asp Arg Thr Cys Ser Tyr Tyr Tyr
                100                 105                 110

Ala Met Asp Val Trp Gly Gln Gly Thr Leu Val Thr Val Ser Ser
            115                 120                 125

<210> SEQ ID NO 131
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone D8

<400> SEQUENCE: 131

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Leu His Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
                100                 105                 110

Ala Met Asp Val Trp Gly Gln Gly Thr Leu Val Thr Val Ser Ser
            115                 120                 125

<210> SEQ ID NO 132
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone E12

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Ser Phe Val Pro Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
                100                 105                 110

Ala Met Asp Val Trp Gly Gln Gly Thr Leu Val Thr Val Ser Ser
            115                 120                 125
```

```
<210> SEQ ID NO 133
<211> LENGTH: 127
<212> TYPE: PRT
<213> ORGANISM: Artificial Sequence
<220> FEATURE:
<223> OTHER INFORMATION: Amino acid sequence of heavy chain variable
      region of affinity matured clone T2A12

<400> SEQUENCE: 133

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly His Gln Gln Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Phe Cys Asn Asp Arg Thr Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 134
<211> LENGTH: 110
<212> TYPE: PRT
<213> ORGANISM: Artificial Sequence
<220> FEATURE:
<223> OTHER INFORMATION: Amino acid sequence of light chain variable
      region of CD19_8.1 antibody

<400> SEQUENCE: 134

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 135
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone 2B1

<400> SEQUENCE: 135

Gln Ser Val Leu Thr Gln Pro Pro Ser Ala Ser Gly Thr Pro Gly Gln
1               5                   10                  15
```

-continued

Arg Val Thr Ile Ser Cys Val Gly Val Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 136
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone B12

<400> SEQUENCE: 136

Gln Ser Val Leu Thr Gln Pro Pro Ser Ala Ser Gly Thr Pro Gly Gln
1               5                   10                  15

Arg Val Thr Ile Ser Cys Ala Gly His Tyr Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 137
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone T2H3

<400> SEQUENCE: 137

Gln Ser Val Leu Thr Gln Pro Pro Ser Ala Ser Gly Thr Pro Gly Gln
1               5                   10                  15

Arg Val Thr Ile Ser Cys Gly Gly Gly Ile Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 138
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone T3C1

<400> SEQUENCE: 138

Gln Ser Val Leu Thr Gln Pro Pro Ser Ala Ser Gly Thr Pro Gly Gln
1               5                   10                  15

Arg Val Thr Ile Ser Cys Ser Gly Pro Ser Asn Ile Gly Ser Asn
            20                  25                  30

Ala Val Tyr Trp Tyr Gln Gln Leu Pro Gly Thr Ala Pro Lys Leu Leu
            35                  40                  45

Ile Tyr Asp Asp Asn His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 139
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone D10

<400> SEQUENCE: 139

Gln Ser Val Leu Thr Gln Pro Pro Ser Ala Ser Gly Thr Pro Gly Gln
1               5                   10                  15

Arg Val Thr Ile Ser Cys Trp Gly Asp Tyr Ser Asn Ile Gly Ser Asn
            20                  25                  30

Ala Val Tyr Trp Tyr Gln Gln Leu Pro Gly Thr Ala Pro Lys Leu Leu
            35                  40                  45

Ile Tyr Asp Asp Asn His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 140
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone F6

<400> SEQUENCE: 140

```
Gln Ser Val Leu Thr Gln Pro Pro Ser Ala Ser Gly Thr Pro Gly Gln
1               5                   10                  15

Arg Val Thr Ile Ser Cys Trp Gly Leu Pro Ser Asn Ile Gly Ser Asn
                20                  25                  30

Ala Val Tyr Trp Tyr Gln Gln Leu Pro Gly Thr Ala Pro Lys Leu Leu
            35                  40                  45

Ile Tyr Asp Asp Asn His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
                100                 105                 110
```

<210> SEQ ID NO 141
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone B2

<400> SEQUENCE: 141

```
Gln Ser Val Leu Thr Gln Pro Pro Ser Ala Ser Gly Thr Pro Gly Gln
1               5                   10                  15

Arg Val Thr Ile Ser Cys Ala Gly Gly Val Ser Asn Ile Gly Ser Asn
                20                  25                  30

Ala Val Tyr Trp Tyr Gln Gln Leu Pro Gly Thr Ala Pro Lys Leu Leu
            35                  40                  45

Ile Tyr Asp Asp Asn His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
                100                 105                 110
```

<210> SEQ ID NO 142
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone B6

<400> SEQUENCE: 142

```
Gln Ser Val Leu Thr Gln Pro Pro Ser Ala Ser Gly Thr Pro Gly Gln
1               5                   10                  15

Arg Val Thr Ile Ser Cys Asn Gly Thr Pro Ser Asn Ile Gly Ser Asn
                20                  25                  30

Ala Val Tyr Trp Tyr Gln Gln Leu Pro Gly Thr Ala Pro Lys Leu Leu
            35                  40                  45

Ile Tyr Asp Asp Asn His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80
```

```
Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110
```

<210> SEQ ID NO 143
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone 2F1

<400> SEQUENCE: 143

```
Gln Ser Val Leu Thr Gln Pro Pro Ser Ala Ser Gly Thr Pro Gly Gln
1               5                   10                  15

Arg Val Thr Ile Ser Cys Tyr Gly Gln Pro Ser Asn Ile Gly Ser Asn
                20                  25                  30

Ala Val Tyr Trp Tyr Gln Gln Leu Pro Gly Thr Ala Pro Lys Leu Leu
            35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110
```

<210> SEQ ID NO 144
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone C8

<400> SEQUENCE: 144

```
Gln Ser Val Leu Thr Gln Pro Pro Ser Ala Ser Gly Thr Pro Gly Gln
1               5                   10                  15

Arg Val Thr Ile Ser Cys Lys Gly Gly Met Ser Asn Ile Gly Ser Asn
                20                  25                  30

Ala Val Tyr Trp Tyr Gln Gln Leu Pro Gly Thr Ala Pro Lys Leu Leu
            35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110
```

<210> SEQ ID NO 145
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone D4

<400> SEQUENCE: 145

Gln Ser Val Leu Thr Gln Pro Pro Ser Ala Ser Gly Thr Pro Gly Gln
1               5                   10                  15

Arg Val Thr Ile Ser Cys Thr Gly Gly Val Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 146
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone B5

<400> SEQUENCE: 146

Gln Ser Val Leu Thr Gln Pro Pro Ser Ala Ser Gly Thr Pro Gly Gln
1               5                   10                  15

Arg Val Thr Ile Ser Cys His Gly Thr Pro Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 147
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone G4

<400> SEQUENCE: 147

Gln Ser Val Leu Thr Gln Pro Pro Ser Ala Ser Gly Thr Pro Gly Gln
1               5                   10                  15

Arg Val Thr Ile Ser Cys Val Gly Lys Pro Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg

```
                65                  70                  75                  80
Ser Glu Asp Glu Ala Asp Tyr Tyr Cys Gly Thr Trp Asp Tyr Ser Leu
                        85                  90                  95

Ser Gly Tyr Val Leu Gly Gly Gly Thr Lys Leu Thr Val Leu
                100                 105                 110

<210> SEQ ID NO 148
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone A7

<400> SEQUENCE: 148

Gln Ser Val Leu Thr Gln Pro Pro Ser Ala Ser Gly Thr Pro Gly Gln
1               5                   10                  15

Arg Val Thr Ile Ser Cys Thr Gly Asn Pro Ser Asn Ile Gly Ser Asn
                20                  25                  30

Ala Val Tyr Trp Tyr Gln Gln Leu Pro Gly Thr Ala Pro Lys Leu Leu
            35                  40                  45

Ile Tyr Asp Asp Asn His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
                100                 105                 110

<210> SEQ ID NO 149
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone D12

<400> SEQUENCE: 149

Gln Ser Val Leu Thr Gln Pro Pro Ser Ala Ser Gly Thr Pro Gly Gln
1               5                   10                  15

Arg Val Thr Ile Ser Cys Arg Gly Ser Ala Ser Asn Ile Gly Ser Asn
                20                  25                  30

Ala Val Tyr Trp Tyr Gln Gln Leu Pro Gly Thr Ala Pro Lys Leu Leu
            35                  40                  45

Ile Tyr Asp Asp Asn His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
                100                 105                 110

<210> SEQ ID NO 150
<211> LENGTH: 110
<212> TYPE: PRT
<213> ORGANISM: Artificial Sequence
<220> FEATURE:
<223> OTHER INFORMATION: Amino acid sequence of light chain variable
``` region of affinity matured clone E2

<400> SEQUENCE: 150

```
Gln Ser Val Leu Thr Gln Pro Pro Ser Ala Ser Gly Thr Pro Gly Gln
1               5                   10                  15

Arg Val Thr Ile Ser Cys Lys Gly Met Ile Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110
```

<210> SEQ ID NO 151
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone T2A1

<400> SEQUENCE: 151

```
Gln Ser Val Leu Thr Gln Pro Pro Ser Ala Ser Gly Thr Pro Gly Gln
1               5                   10                  15

Arg Val Thr Ile Ser Cys Ala Gly Lys Pro Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110
```

<210> SEQ ID NO 152
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone T3H9

<400> SEQUENCE: 152

```
Gln Ser Val Leu Thr Gln Pro Pro Ser Ala Ser Gly Thr Pro Gly Gln
1               5                   10                  15

Arg Val Thr Ile Ser Cys Ser Gly Met Leu Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60
```

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 153
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone 2G1

<400> SEQUENCE: 153

Gln Ser Val Leu Thr Gln Pro Pro Ser Ala Ser Gly Thr Pro Gly Gln
1               5                   10                  15

Arg Val Thr Ile Ser Cys Lys Gly Ser Phe Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 154
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone C4

<400> SEQUENCE: 154

Gln Ser Val Leu Thr Gln Pro Pro Ser Ala Ser Gly Thr Pro Gly Gln
1               5                   10                  15

Arg Val Thr Ile Ser Cys Gly Gly Gln Pro Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 155
<211> LENGTH: 110
<212> TYPE: PRT
<213> ORGANISM: Artificial Sequence

```
<220> FEATURE:
<223> OTHER INFORMATION: Amino acid sequence of light chain variable
      region of affinity matured clone C5

<400> SEQUENCE: 155

Gln Ser Val Leu Thr Gln Pro Pro Ser Ala Ser Gly Thr Pro Gly Gln
1               5                   10                  15

Arg Val Thr Ile Ser Cys Lys Gly Gly Met Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 156
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone D1

<400> SEQUENCE: 156

Gln Ser Val Leu Thr Gln Pro Pro Ser Ala Ser Gly Thr Pro Gly Gln
1               5                   10                  15

Arg Val Thr Ile Ser Cys Ser Gly Gly Pro Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 157
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone D2

<400> SEQUENCE: 157

Gln Ser Val Leu Thr Gln Pro Pro Ser Ala Ser Gly Thr Pro Gly Gln
1               5                   10                  15

Arg Val Thr Ile Ser Cys Gln Gly Gln Pro Ser Asn Ile Gly Ser Asn
            20                  25                  30

Ala Val Tyr Trp Tyr Gln Gln Leu Pro Gly Thr Ala Pro Lys Leu Leu
        35                  40                  45
```

Ile Tyr Asp Asp Asn His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Thr Trp Asp Tyr Ser Leu
                 85                  90                  95

Ser Gly Tyr Val Leu Gly Gly Gly Thr Lys Leu Thr Val Leu
            100                 105                 110

<210> SEQ ID NO 158
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone E1

<400> SEQUENCE: 158

Gln Ser Val Leu Thr Gln Pro Pro Ser Ala Ser Gly Thr Pro Gly Gln
 1               5                  10                  15

Arg Val Thr Ile Ser Cys Thr Gly Asn Pro Ser Asn Ile Gly Ser Asn
                 20                  25                  30

Ala Val Tyr Trp Tyr Gln Gln Leu Pro Gly Thr Ala Pro Lys Leu Leu
             35                  40                  45

Ile Tyr Asp Asp Asn His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Thr Trp Asp Tyr Ser Leu
                 85                  90                  95

Ser Gly Tyr Val Leu Gly Gly Gly Thr Lys Leu Thr Val Leu
            100                 105                 110

<210> SEQ ID NO 159
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone F3

<400> SEQUENCE: 159

Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Ser Ala
                 20                  25                  30

Pro Leu Tyr Trp Tyr Gln Gln Leu Pro Gly Thr Ala Pro Lys Leu Leu
             35                  40                  45

Ile Tyr Asp Asp Asn His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Thr Trp Asp Tyr Ser Leu
                 85                  90                  95

Ser Gly Tyr Val Leu Gly Gly Gly Thr Lys Leu Thr Val Leu
            100                 105                 110

<210> SEQ ID NO 160
<211> LENGTH: 110

<212> TYPE: PRT
<213> ORGANISM: Artificial Sequence
<220> FEATURE:
<223> OTHER INFORMATION: Amino acid sequence of light chain variable
      region of affinity matured clone T2C1

<400> SEQUENCE: 160

Gln Ser Val Leu Thr Gln Pro Pro Ser Ala Ser Gly Thr Pro Gly Gln
1               5                   10                  15

Arg Val Thr Ile Ser Cys Arg Gly Gly Pro Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
                100                 105                 110

<210> SEQ ID NO 161
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone T2H1

<400> SEQUENCE: 161

Gln Ser Val Leu Thr Gln Pro Pro Ser Ala Ser Gly Thr Pro Gly Gln
1               5                   10                  15

Arg Val Thr Ile Ser Cys Gln Gly Gly Tyr Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
                100                 105                 110

<210> SEQ ID NO 162
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone T2H5

<400> SEQUENCE: 162

Gln Ser Val Leu Thr Gln Pro Pro Ser Ala Ser Gly Thr Pro Gly Gln
1               5                   10                  15

Arg Val Thr Ile Ser Cys Ser Gly Asn Pro Ser Asn Ile Gly Ser Asn
            20                  25                  30

Ala Val Tyr Trp Tyr Gln Gln Leu Pro Gly Thr Ala Pro Lys Leu Leu

```
                35                  40                  45
Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 163
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone T3B8

<400> SEQUENCE: 163

Gln Ser Val Leu Thr Gln Pro Pro Ser Ala Ser Gly Thr Pro Gly Gln
1               5                   10                  15

Arg Val Thr Ile Ser Cys Glu Gly Ser Pro Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 164
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone A12

<400> SEQUENCE: 164

Gln Ser Val Leu Thr Gln Pro Pro Ser Ala Ser Gly Thr Pro Gly Gln
1               5                   10                  15

Arg Val Thr Ile Ser Cys Gln Gly Pro Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110
```

```
<210> SEQ ID NO 165
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone C2

<400> SEQUENCE: 165

Gln Ser Val Leu Thr Gln Pro Pro Ser Ala Ser Gly Thr Pro Gly Gln
1               5                   10                  15

Arg Val Thr Ile Ser Cys Thr Gly Gly Leu Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 166
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone D7

<400> SEQUENCE: 166

Gln Ser Val Leu Thr Gln Pro Pro Ser Ala Ser Gly Thr Pro Gly Gln
1               5                   10                  15

Arg Val Thr Ile Ser Cys Glu Gly Gln Pro Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 167
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone E3

<400> SEQUENCE: 167

Gln Ser Val Leu Thr Gln Pro Pro Ser Ala Ser Gly Thr Pro Gly Gln
1               5                   10                  15

Arg Val Thr Ile Ser Cys Ser Gly Gly Tyr Ser Asn Ile Gly Ser Asn
            20                  25                  30
```

```
Ala Val Tyr Trp Tyr Gln Gln Leu Pro Gly Thr Ala Pro Lys Leu Leu
            35                  40                  45

Ile Tyr Asp Asp Asn His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Thr Trp Asp Tyr Ser Leu
                 85                  90                  95

Ser Gly Tyr Val Leu Gly Gly Gly Thr Lys Leu Thr Val Leu
                100                 105                 110

<210> SEQ ID NO 168
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone H10

<400> SEQUENCE: 168

Gln Ser Val Leu Thr Gln Pro Pro Ser Ala Ser Gly Thr Pro Gly Gln
 1               5                  10                  15

Arg Val Thr Ile Ser Cys Leu Gly Gly Tyr Ser Asn Ile Gly Ser Asn
                 20                  25                  30

Ala Val Tyr Trp Tyr Gln Gln Leu Pro Gly Thr Ala Pro Lys Leu Leu
            35                  40                  45

Ile Tyr Asp Asp Asn His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Thr Trp Asp Tyr Ser Leu
                 85                  90                  95

Ser Gly Tyr Val Leu Gly Gly Gly Thr Lys Leu Thr Val Leu
                100                 105                 110

<210> SEQ ID NO 169
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone T3F5

<400> SEQUENCE: 169

Gln Ser Val Leu Thr Gln Pro Pro Ser Ala Ser Gly Thr Pro Gly Gln
 1               5                  10                  15

Arg Val Thr Ile Ser Cys His Gly Gln Pro Ser Asn Ile Gly Ser Asn
                 20                  25                  30

Ala Val Tyr Trp Tyr Gln Gln Leu Pro Gly Thr Ala Pro Lys Leu Leu
            35                  40                  45

Ile Tyr Asp Asp Asn His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Thr Trp Asp Tyr Ser Leu
                 85                  90                  95

Ser Gly Tyr Val Leu Gly Gly Gly Thr Lys Leu Thr Val Leu
                100                 105                 110
```

<210> SEQ ID NO 170
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone A10

<400> SEQUENCE: 170

Gln Ser Val Leu Thr Gln Pro Pro Ser Ala Ser Gly Thr Pro Gly Gln
1               5                   10                  15

Arg Val Thr Ile Ser Cys Ser Gly Asp Pro Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 171
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone T3H1

<400> SEQUENCE: 171

Gln Ser Val Leu Thr Gln Pro Pro Ser Ala Ser Gly Thr Pro Gly Gln
1               5                   10                  15

Arg Val Thr Ile Ser Cys Asp Gly Gly Tyr Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 172
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone B1

<400> SEQUENCE: 172

Gln Ser Val Leu Thr Gln Pro Pro Ser Ala Ser Gly Thr Pro Gly Gln
1               5                   10                  15

Arg Val Thr Ile Ser Cys Val Gly Ser Pro Ser Asn Ile Gly Ser Asn
            20                  25                  30

Ala Val Tyr Trp Tyr Gln Gln Leu Pro Gly Thr Ala Pro Lys Leu Leu
                35                  40                  45

Ile Tyr Asp Asp Asn His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 173
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone B7

<400> SEQUENCE: 173

Gln Ser Val Leu Thr Gln Pro Pro Ser Ala Ser Gly Thr Pro Gly Gln
1               5                   10                  15

Arg Val Thr Ile Ser Cys Arg Gly Thr Pro Ser Asn Ile Gly Ser Asn
            20                  25                  30

Ala Val Tyr Trp Tyr Gln Gln Leu Pro Gly Thr Ala Pro Lys Leu Leu
                35                  40                  45

Ile Tyr Asp Asp Asn His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 174
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone D8

<400> SEQUENCE: 174

Gln Ser Val Leu Thr Gln Pro Pro Ser Ala Ser Gly Thr Pro Gly Gln
1               5                   10                  15

Arg Val Thr Ile Ser Cys Val Gly Asn Leu Ser Asn Ile Gly Ser Asn
            20                  25                  30

Ala Val Tyr Trp Tyr Gln Gln Leu Pro Gly Thr Ala Pro Lys Leu Leu
                35                  40                  45

Ile Tyr Asp Asp Asn His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

```
Ser Gly Tyr Val Leu Gly Gly Gly Thr Lys Leu Thr Val Leu
            100                 105                 110

<210> SEQ ID NO 175
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone E12

<400> SEQUENCE: 175

Gln Ser Val Leu Thr Gln Pro Pro Ser Ala Ser Gly Thr Pro Gly Gln
1               5                   10                  15

Arg Val Thr Ile Ser Cys Ala Gly Ser Ala Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 176
<211> LENGTH: 110
<212> TYPE: PRT
<213> ORGANISM: Artificial Sequence
<220> FEATURE:
<223> OTHER INFORMATION: Amino acid sequence of light chain variable
      region of affinity matured clone T2A12

<400> SEQUENCE: 176

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Ala
            20                  25                  30

Pro Thr Tyr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Leu Gly Gly Gly Thr Lys Leu Thr Val Leu
            100                 105                 110

<210> SEQ ID NO 177
<211> LENGTH: 60
<212> TYPE: DNA
<213> ORGANISM: Artificial Sequence
<220> FEATURE:
<223> OTHER INFORMATION: Nucleotide sequence for encoding CD8 leader

<400> SEQUENCE: 177
atggccctgc ctgtgaccgc tctgctgctg cccctggctc tgctgctgca cgccgctcgc       60
```

<210> SEQ ID NO 178
<211> LENGTH: 207
<212> TYPE: DNA
<213> ORGANISM: Artificial Sequence
<220> FEATURE:
<223> OTHER INFORMATION: Nucleotide sequence for encoding CD8
      hinge/transmembrain domain

<400> SEQUENCE: 178
accacaactc cagctccccg gcccctacc cctgcaccaa caatcgccag ccagcctctg      60
tccctgagac cagaggcatg taggccagct gcaggaggag cagtgcatac aagaggcctg    120
gacttcgcct gcgatatcta catttgggcc cctctggcag gaacttgtgg cgtgctgctg    180
ctgtctctgg tcatcaccct gtactgc                                       207

<210> SEQ ID NO 179
<211> LENGTH: 126
<212> TYPE: DNA
<213> ORGANISM: Artificial Sequence
<220> FEATURE:
<223> OTHER INFORMATION: Nucleotide sequence for encoding intracellular
      domain of CD137

<400> SEQUENCE: 179
aaaaggggcc gcaagaaact gctgtatatt ttcaagcagc ccttcatgcg gcccgtgcag     60
accacacagg aggaagacgg tgctcctgt agattccccg aggaagagga aggcgggtgt    120
gagctg                                                              126

<210> SEQ ID NO 180
<211> LENGTH: 336
<212> TYPE: DNA
<213> ORGANISM: Artificial Sequence
<220> FEATURE:
<223> OTHER INFORMATION: Nucleotide sequence for encoding intracellular
      domain of CD3-zeta

<400> SEQUENCE: 180
cgcgtcaagt tcagccgatc agccgatgct cctgcataca agcagggcca gaatcagctg     60
tataacgagc tgaatctggg gcgccgagag gaatacgacg tgctggataa gcggagaggg    120
agggaccccg aaatgggagg caaacctagg cgcaagaacc cacaggaggg actgtacaat    180
gaactgcaga aggacaaaat ggccgaggct tattccgaaa ttgggatgaa aggagagcga    240
cggagaggga agggacacga tgggctgtat cagggactgt ctaccgccac taaagatacc    300
tacgacgctc tgcacatgca ggctctgcca cctcgc                             336

<210> SEQ ID NO 181
<211> LENGTH: 1518
<212> TYPE: DNA
<213> ORGANISM: Artificial Sequence
<220> FEATURE:
<223> OTHER INFORMATION: Nucleotide sequence of CAR construct comprising
      CD19_8.1 scFv

<400> SEQUENCE: 181
atggccctgc ctgtgaccgc tctgctgctg cccctggctc tgctgctgca cgccgctcgc     60
cccgtggccc aggcggccga ggtgcagctg ttggagtctg ggggaggctt ggtacagcct    120
ggggggtccc tgagactctc ctgtgcagcc tctggattca cctttagcga ttattatatg    180
agctgggtcc gccaggctcc agggaagggg ctggagtggg tctcaggat ctattatgat    240 gatagtagtc aatattacgc tgattctgta aaaggtcggt tcaccatctc cagagacaat    300

```
tccaagaaca cgctgtatct gcaaatgaac agcctgagag ccgaggacac ggccgtgtat    360
tactgtgcga aggtcctct tttttgtaat gatcggactt gttcttatta ttatgctatg    420
gacgtctggg gccagggtac actggtcacc gtgagctcag gtggaggcgg ttcaggcgga    480
ggtggatccg gcggtggcgg atcgcagtct gtgctgactc agccaccctc agcgtctggg    540 accccgggc agagggtcac catctcttgt actggctctt catctaatat tggcagtaat    600
gctgtctact ggtaccagca gctaccagga acggccccca aactcctcat ctatgatgat    660
aatcatcggc caagcggggt ccctgaccga ttctctggct ccaagtctgg cacctcagcc    720
tccctggcca tcagtgggct ccggtccgag gatgaggctg attattactg tggtacctgg    780
gattatagcc tgagtggtta tgtcttaggc ggaggcacca gctgacggt cctaggccag    840 gccggccaga ccacaactcc agctccccgg ccccctaccc ctgcaccaac aatcgccagc    900
cagcctctgt ccctgagacc agaggcatgt aggccagctg caggaggagc agtgcataca    960
agaggcctgg acttcgcctg cgatatctac atttgggctc ctctggcagg aacttgtggc   1020
gtgctgctgc tgtctctggt catcaccctg tactgcaaaa ggggccgcaa gaaactgctg   1080 tatatttca gcagcccctt catgcggccc gtgcagacca cacaggagga agacgggtgc   1140
tcctgtagat ccccgagga agaggaaggc gggtgtgagc tgcgcgtcaa gttcagccga   1200
tcagccgatg ctcctgcata caagcagggc cagaatcagc tgtataacga gctgaatctg   1260 ggcgccgag aggaatacga cgtgctggat aagcggagag ggagggaccc cgaaatggga   1320
ggcaaaccta ggcgcaagaa cccacaggag ggactgtaca atgaactgca gaaggacaaa   1380
atggccgagg cttattccga aattgggatg aaggagagc gacggagagg gaagggacac   1440
gatgggctgt atcagggact gtctaccgcc actaaagata cctacgacgc tctgcacatg   1500
caggctctgc cacctcgc                                                 1518
```

<210> SEQ ID NO 182
<211> LENGTH: 15
<212> TYPE: DNA
<213> ORGANISM: Artificial Sequence
<220> FEATURE:
<223> OTHER INFORMATION: Nucleotide sequence for encoding CDRH1 of
      CD19_8.1 antibody

<400> SEQUENCE: 182

```
gattattata tgagc                                                      15
```

<210> SEQ ID NO 183
<211> LENGTH: 51
<212> TYPE: DNA
<213> ORGANISM: Artificial Sequence
<220> FEATURE:
<223> OTHER INFORMATION: Nucleotide sequence for encoding CDRH2 of
      CD19_8.1 antibody

<400> SEQUENCE: 183

```
gggatctatt atgatgatag tagtcaatat tacgctgatt ctgtaaaagg t             51
```

<210> SEQ ID NO 184
<211> LENGTH: 54
<212> TYPE: DNA
<213> ORGANISM: Artificial Sequence
<220> FEATURE:
<223> OTHER INFORMATION: Nucleotide sequence for encoding CDRH3 of
      CD19_8.1 antibody

<400> SEQUENCE: 184

```
ggtcctcttt tttgtaatga tcggacttgt tcttattatt atgctatgga cgtc          54
```

<210> SEQ ID NO 185
<211> LENGTH: 39
<212> TYPE: DNA
<213> ORGANISM: Artificial Sequence
<220> FEATURE:
<223> OTHER INFORMATION: Nucleotide sequence for encoding CDRL1 of
      CD19_8.1 antibody

<400> SEQUENCE: 185

```
actggctctt catctaatat tggcagtaat gctgtctac                            39
```

<210> SEQ ID NO 186
<211> LENGTH: 21
<212> TYPE: DNA
<213> ORGANISM: Artificial Sequence
<220> FEATURE:
<223> OTHER INFORMATION: Nucleotide sequence for encoding CDRL2 of
      CD19_8.1 antibody

<400> SEQUENCE: 186

```
gatgataatc atcggccaag c                                              21
```

<210> SEQ ID NO 187
<211> LENGTH: 33
<212> TYPE: DNA
<213> ORGANISM: Artificial Sequence
<220> FEATURE:
<223> OTHER INFORMATION: Nucleotide sequence for encoding CDRL3 of
      CD19_8.1 antibody

<400> SEQUENCE: 187

```
ggtacctggg attatagcct gagtggttat gtc                                 33
```

<210> SEQ ID NO 188
<211> LENGTH: 381
<212> TYPE: DNA
<213> ORGANISM: Artificial Sequence
<220> FEATURE:
<223> OTHER INFORMATION: Nucleotide sequence for encoding heavy chain
      variable region of CD19_8.1 antibody

<400> SEQUENCE: 188

```
gaggtgcagc tgttggagtc tgggggaggc ttggtacagc ctggggggtc cctgagactc    60
tcctgtgcag cctctggatt cacctttagc gattattata tgagctgggt ccgccaggct    120
ccagggaagg gctggagtg gtctcaggg atctattatg atgatagtag tcaatattac      180
gctgattctg taaaaggtcg gttcaccatc tccagagaca attccaagaa cacgctgtat    240
ctgcaaatga acagcctgag agccgaggac acggccgtgt attactgtgc gaaaggtcct    300
cttttttgta atgatcggac ttgttcttat tattatgcta tggacgtctg gggccagggt    360
acactggtca ccgtgagctc a                                              381
```

<210> SEQ ID NO 189
<211> LENGTH: 330
<212> TYPE: DNA
<213> ORGANISM: Artificial Sequence
<220> FEATURE:
<223> OTHER INFORMATION: Nucleotide sequence for encoding light chain
      variable region of CD19_8.1 antibody

<400> SEQUENCE: 189

```
cagtctgtgc tgactcagcc accctcagcg tctgggaccc ccgggcagag ggtcaccatc    60
```

```
tcttgtactg gctcttcatc taatattggc agtaatgctg tctactggta ccagcagcta      120
ccaggaacgg ccccaaaact cctcatctat gatgataatc atcggccaag cggggtccct     180
gaccgattct ctggctccaa gtctggcacc tcagcctccc tggccatcag tgggctccgg      240
tccgaggatg aggctgatta ttactgtggt acctgggatt atagcctgag tggttatgtc      300
ttaggcggag gcaccaagct gacggtccta                                      330
```

<210> SEQ ID NO 190
<211> LENGTH: 17
<212> TYPE: PRT
<213> ORGANISM: Artificial Sequence
<220> FEATURE:
<223> OTHER INFORMATION: CDRH2 of CD19_8.1_3C12, 6F10, 7D2, 7H11, 8E8, 10D3, 10E5, 10H4

<400> SEQUENCE: 190

Gly Ile Tyr Tyr Asp Gly Ser Ala Lys Tyr Tyr Ala Asp Ser Val Lys
1               5                   10                  15

Gly

<210> SEQ ID NO 191
<211> LENGTH: 18
<212> TYPE: PRT
<213> ORGANISM: Artificial Sequence
<220> FEATURE:
<223> OTHER INFORMATION: CDRH3 of CD19_8.1_3C12

<400> SEQUENCE: 191

Gly Pro Asn Phe Cys Asn Asp Arg Thr Cys Ser Tyr Tyr Tyr Ala Met
1               5                   10                  15

Asp Val

<210> SEQ ID NO 192
<211> LENGTH: 18
<212> TYPE: PRT
<213> ORGANISM: Artificial Sequence
<220> FEATURE:
<223> OTHER INFORMATION: CDRH3 of CD19_8.1_6F10

<400> SEQUENCE: 192

Gly Pro Leu Phe Cys Asn Asp Arg Thr Cys Ser Tyr Tyr Tyr Ala Met
1               5                   10                  15

Asp Val

<210> SEQ ID NO 193
<211> LENGTH: 18
<212> TYPE: PRT
<213> ORGANISM: Artificial Sequence
<220> FEATURE:
<223> OTHER INFORMATION: CDRH3 of CD19_8.1_7D2

<400> SEQUENCE: 193

Gly Pro Leu Phe Cys Asn Asp Asn Thr Cys Ser Tyr Tyr Tyr Ala Met
1               5                   10                  15

Asp Val

<210> SEQ ID NO 194
<211> LENGTH: 18
<212> TYPE: PRT
<213> ORGANISM: Artificial Sequence
<220> FEATURE:
<223> OTHER INFORMATION: CDRH3 of CD19_8.1_7H11

<400> SEQUENCE: 194

Gly Pro Leu Phe Cys Asn Asp Asp Thr Cys Ser Tyr Tyr Tyr Ala Met
1               5                   10                  15
Asp Val

<210> SEQ ID NO 195
<211> LENGTH: 18
<212> TYPE: PRT
<213> ORGANISM: Artificial Sequence
<220> FEATURE:
<223> OTHER INFORMATION: CDRH3 of CD19_8.1_8E8

<400> SEQUENCE: 195

Gly Pro Leu Phe Cys Asn Asp Arg Asp Cys Ser Tyr Tyr Tyr Ala Met
1               5                   10                  15
Asp Val

<210> SEQ ID NO 196
<211> LENGTH: 18
<212> TYPE: PRT
<213> ORGANISM: Artificial Sequence
<220> FEATURE:
<223> OTHER INFORMATION: CDRH3 of CD19_8.1_10D3

<400> SEQUENCE: 196

Gly Pro Leu Phe Cys Asn Asp Arg Thr Cys Ser Met Tyr Tyr Ala Met
1               5                   10                  15
Asp Val

<210> SEQ ID NO 197
<211> LENGTH: 18
<212> TYPE: PRT
<213> ORGANISM: Artificial Sequence
<220> FEATURE:
<223> OTHER INFORMATION: CDRH3 of CD19_8.1_10E5

<400> SEQUENCE: 197

Gly Pro Leu Phe Cys Asn Asp Arg Thr Cys Ser Met Tyr Tyr Ala Met
1               5                   10                  15
Asp Val

<210> SEQ ID NO 198
<211> LENGTH: 18
<212> TYPE: PRT
<213> ORGANISM: Artificial Sequence
<220> FEATURE:
<223> OTHER INFORMATION: CDRH3 of CD19_8.1_10H4

<400> SEQUENCE: 198

Gly Pro Leu Phe Cys Asn Asp Arg Thr Cys Ser Lys Tyr Tyr Ala Met
1               5                   10                  15
Asp Val

<210> SEQ ID NO 199
<211> LENGTH: 13
<212> TYPE: PRT
<213> ORGANISM: Artificial Sequence
<220> FEATURE:
<223> OTHER INFORMATION: CDRL1 of CD19_8.1_3C12, 6F10, 7D2, 7H11, 8E8,
      10E5, 10H4

<400> SEQUENCE: 199

```
Tyr Gly Gln Pro Ser Asn Ile Gly Ser Asn Ala Val Tyr
1               5                   10
```

<210> SEQ ID NO 200
<211> LENGTH: 13
<212> TYPE: PRT
<213> ORGANISM: Artificial Sequence
<220> FEATURE:
<223> OTHER INFORMATION: CDRL1 of CD19_8.1_10D3

<400> SEQUENCE: 200

```
Thr Gly Gly Pro Ser Asn Ile Gly Ser Asn Ala Val Tyr
1               5                   10
```

<210> SEQ ID NO 201
<211> LENGTH: 17
<212> TYPE: PRT
<213> ORGANISM: Artificial Sequence
<220> FEATURE:
<223> OTHER INFORMATION: General Formula 1
<220> FEATURE:
<221> NAME/KEY: MISC_FEATURE
<222> LOCATION: (6)..(6)
<223> OTHER INFORMATION: Xaa is Gly, Ala, or Ser
<220> FEATURE:
<221> NAME/KEY: MISC_FEATURE
<222> LOCATION: (7)..(7)
<223> OTHER INFORMATION: Xaa is Ser, Thr, Ile, Ala, Asp, Phe, Leu, or
      His
<220> FEATURE:
<221> NAME/KEY: MISC_FEATURE
<222> LOCATION: (8)..(8)
<223> OTHER INFORMATION: Xaa is Ala, Thr, Ser, Gln, Trp, Ile, Val, Met,
      Asn, Tyr, or His
<220> FEATURE:
<221> NAME/KEY: MISC_FEATURE
<222> LOCATION: (9)..(9)
<223> OTHER INFORMATION: Xaa is Arg, Lys Ser, Val, Ala, Gln, Leu, Thr,
      Glu, Asp, Met, Leu, Phe, or Pro
<220> FEATURE:
<221> NAME/KEY: MISC_FEATURE
<222> LOCATION: (10)..(10)
<223> OTHER INFORMATION: Xaa is Tyr, Gly, Ser, or Thr
<220> FEATURE:
<221> NAME/KEY: MISC_FEATURE
<222> LOCATION: (11)..(11)
<223> OTHER INFORMATION: Xaa is Tyr, Trp, Met, or Leu
<220> FEATURE:
<221> NAME/KEY: MISC_FEATURE
<222> LOCATION: (12)..(12)
<223> OTHER INFORMATION: Xaa is Ala, Ser, Thr, or Leu
<220> FEATURE:
<221> NAME/KEY: MISC_FEATURE
<222> LOCATION: (13)..(13)
<223> OTHER INFORMATION: Xaa is Asp, Ser, Gly, Asn, or Pro

<400> SEQUENCE: 201

```
Gly Ile Tyr Tyr Asp Xaa Xaa Xaa Xaa Xaa Xaa Xaa Xaa Ser Val Lys
1               5                   10                  15

Gly
```

<210> SEQ ID NO 202
<211> LENGTH: 13
<212> TYPE: PRT
<213> ORGANISM: Artificial Sequence
<220> FEATURE:
<223> OTHER INFORMATION: General Formula 2
<220> FEATURE:
<221> NAME/KEY: MISC_FEATURE
<222> LOCATION: (1)..(1)
<223> OTHER INFORMATION: Xaa is Val, Ala, Gly, Ser, Trp, Asn, Tyr, Lys,
      Thr, His, Arg, Gln, Glu, or Asp
<220> FEATURE:

-continued

```
<221> NAME/KEY: MISC_FEATURE
<222> LOCATION: (3)..(3)
<223> OTHER INFORMATION: Xaa is Gly, His, Asp, Leu, Thr, Gln, Lys, Asn,
      Ser, or Met
<220> FEATURE:
<221> NAME/KEY: MISC_FEATURE
<222> LOCATION: (4)..(4)
<223> OTHER INFORMATION: Xaa is Val, Tyr, Ile, Pro, Val, Met, Ala, Leu,
      Phe, or Ser
<220> FEATURE:
<221> NAME/KEY: MISC_FEATURE
<222> LOCATION: (10)..(10)
<223> OTHER INFORMATION: Xaa is Asn or Ala
<220> FEATURE:
<221> NAME/KEY: MISC_FEATURE
<222> LOCATION: (11)..(11)
<223> OTHER INFORMATION: Xaa is Ala or Pro
<220> FEATURE:
<221> NAME/KEY: MISC_FEATURE
<222> LOCATION: (12)..(12)
<223> OTHER INFORMATION: Xaa is Val, Thr, or Leu

<400> SEQUENCE: 202

Xaa Gly Xaa Xaa Ser Asn Ile Gly Ser Xaa Xaa Xaa Tyr
1               5                   10

<210> SEQ ID NO 203
<211> LENGTH: 17
<212> TYPE: PRT
<213> ORGANISM: Artificial Sequence
<220> FEATURE:
<223> OTHER INFORMATION: General Formula 1-1
<220> FEATURE:
<221> NAME/KEY: MISC_FEATURE
<222> LOCATION: (6)..(6)
<223> OTHER INFORMATION: Xaa is Gly, Ala, or Ser
<220> FEATURE:
<221> NAME/KEY: MISC_FEATURE
<222> LOCATION: (7)..(7)
<223> OTHER INFORMATION: Xaa is Ser, Thr, Ile, Ala, Asp, Phe, Leu, or
      His
<220> FEATURE:
<221> NAME/KEY: MISC_FEATURE
<222> LOCATION: (8)..(8)
<223> OTHER INFORMATION: Xaa is Ala, Thr, Ser, Gln, Trp, Ile, Val, Met,
      Asn, Tyr, or His
<220> FEATURE:
<221> NAME/KEY: MISC_FEATURE
<222> LOCATION: (9)..(9)
<223> OTHER INFORMATION: Xaa is Arg, Lys, Ser, Val, Ala, Gln, Leu, Thr,
      Glu, Asp, Met, Leu, Phe, or Pro

<400> SEQUENCE: 203

Gly Ile Tyr Tyr Asp Xaa Xaa Xaa Xaa Tyr Tyr Ala Asp Ser Val Lys
1               5                   10                  15

Gly

<210> SEQ ID NO 204
<211> LENGTH: 13
<212> TYPE: PRT
<213> ORGANISM: Artificial Sequence
<220> FEATURE:
<223> OTHER INFORMATION: General Formula 2-1
<220> FEATURE:
<221> NAME/KEY: MISC_FEATURE
<222> LOCATION: (1)..(1)
<223> OTHER INFORMATION: Xaa is Val, Ala, Gly, Ser, Trp, Asn, Tyr, Lys,
      Thr, His, Arg, Gln, Glu, or Asp
<220> FEATURE:
<221> NAME/KEY: MISC_FEATURE
<222> LOCATION: (3)..(3)
<223> OTHER INFORMATION: Xaa is Gly, His, Asp, Leu, Thr, Gln, Lys, Asn,
      Ser, or Met
<220> FEATURE:
```

```
<221> NAME/KEY: MISC_FEATURE
<222> LOCATION: (4)..(4)
<223> OTHER INFORMATION: Xaa is Val, Tyr, Ile, Pro, Val, Met, Ala, Leu,
      Ile, Phe, or Ser

<400> SEQUENCE: 204

Xaa Gly Xaa Xaa Ser Asn Ile Gly Ser Asn Ala Val Tyr
1               5                   10
```